(12) United States Patent
Wang

(10) Patent No.: US 10,100,373 B2
(45) Date of Patent: Oct. 16, 2018

(54) MULTIPLEX ASSAY FOR THE DETECTION OF CITRUS PATHOGENS

(71) Applicant: The Regents of the University of California, Oakland, CA (US)

(72) Inventor: Jinbo Wang, Berwyn Heights, MD (US)

(73) Assignee: The Regents of the University of California, Oakland, CA (US)

( * ) Notice: Subject to any disclaimer, the term of this patent is extended or adjusted under 35 U.S.C. 154(b) by 178 days.

(21) Appl. No.: 15/162,045

(22) Filed: May 23, 2016

(65) Prior Publication Data

US 2016/0258030 A1 Sep. 8, 2016

Related U.S. Application Data

(62) Division of application No. 13/945,350, filed on Jul. 18, 2013, now Pat. No. 9,347,106.

(60) Provisional application No. 61/673,090, filed on Jul. 18, 2012.

(51) Int. Cl.
*C12Q 1/68* (2018.01)
*C12Q 1/70* (2006.01)

(52) U.S. Cl.
CPC ......... *C12Q 1/701* (2013.01); *C12Q 2600/16* (2013.01)

(58) Field of Classification Search
None
See application file for complete search history.

(56) References Cited

U.S. PATENT DOCUMENTS

2007/0015188 A1 1/2007 Luo et al.

OTHER PUBLICATIONS

Weng et al. (Persistent Infection and Promiscuous Recombination of Multiple Genotypes of an RNA Virus within a Single Host Generate Extensive Diversity, PLoS One. Sep. 19, 2007;2(9):e917).*
Xiong et al. (Designing and Testing of a Citrus tristeza virus Resequencing Microarray, Proceedings of the International Organization of Citrus Virologists. 2006;16:11-22).*
Stewart (Strain differentiation of Citrus tristeza virus isolates from South Africa by PCR and microarray, Masters Thesis, University of Pretoria, Natural and Agricultural Science, Nov. 2006).*
Ito et al. (Simultaneous detection of six citrus viroids and Apple stem grooving virus from citrus plants by multiplex reverse transcription polymerase chain reaction, J Virol Methods. Dec. 2002;106(2):235-9).*
Roy et al. (A multiplex polymerase chain reaction method for reliable, sensitive and simultaneous detection of multiple viruses in citrus trees, J Virol Methods. Oct. 2005;129(1):47-55).*
Weng et al., "Persistent Infection and Promiscuous Recombination of Multiple Genotypes of an RNA Virus within a Single Host Generate Extensive Diversity," *PLoS One.* Sep. 19, 2007;2(9):e917).
Xiong et al., "Designing and Testing of a Citrus tristeza virus Resequencing Microarray," *Proceedings of the International Organization of Citrus Virologists.* 2006;16:11-22).
Stewart, "Strain differentiation of Citrus tristeza virus isolates from South Africa by PCR and microarray," *Masters Thesis, University of Pretoria, Natural and Agricultural Science,* Nov. 2006).
NCBI Accession No. EU937519 (attached, Sep. 9, 2008).
Flagella et al., "A multiplex branched DNA assay for parallel quantitative gene expression profiling," *Anal Biochem.* May 1, 2006;352(1 ):50-60. (Epub Mar. 2, 2006).
Saponari et al., "Quantitative detection of Citrus tristeza virus in citrus and aphids by real-time reverse transcription-PeR(TaqMan," *J Virol Methods*Jan. 2008;147(1):43-53. Epub Sep. 20, 2007).
NCBI Accession No. 037958 (attached, Jan. 24, 2007).
NCBI Accession No. AF260651 (attached, Jul. 14, 2000).

* cited by examiner

*Primary Examiner* — Aaron A Priest
(74) *Attorney, Agent, or Firm* — Kilpatrick Townsend & Stockton LLP

(57) ABSTRACT

The present invention provides methods and compositions for detecting multiple citrus pathogens using a multiplex branched DNA signal amplification reaction.

12 Claims, 3 Drawing Sheets

Specification includes a Sequence Listing.

MULTIPLEX ASSAY FOR THE DETECTION OF CITRUS PATHOGENS

CROSS-REFERENCE TO RELATED APPLICATIONS

This application is a divisional application of U.S. application Ser. No. 13/945,350, filed Jul. 18, 2013, which claims priority benefit to U.S. provisional application No. 61/673,090, filed Jul. 18, 2012. Each application is herein incorporated by reference for all purposes.

STATEMENT OF GOVERNMENTAL SUPPORT

This invention was made with Government support under Grant Nos. 58-5302-1-119 and 58-5302-1-226, awarded by the U.S. Department of Agriculture. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file—SEQUENCE-DIV.TXT, created on May 23, 2016, 53,825 bytes, machine format IBM-PC, MS-Windows operating system, is incorporated by reference for all purposes.

BACKGROUND OF THE INVENTION

Citrus is susceptible to numerous disease caused by plant pathogens. There is a need for efficient and sensitive methods of detecting pathogens.

The method of the present invention provides a method for the detection of nine citrus pathogens in a single sample using a multiplex branched signal amplification reaction. The present invention thus provides an accurate, efficient, and quick method of detecting multiple citrus pathogens that is also suitable for high throughput screenings.

BRIEF SUMMARY OF THE INVENTION

The present invention provides methods and kits for detecting up to nine citrus pathogens where the pathogens are Citrus tristeza virus (CTV) universal, CTV genotype T30 and CTV genotype VT; Citrus psorosis virus (CPsV); Citrus tatter leaf virus (CTLV); Citrus leaf blotch virus (CLBV); Citrus exocortis viroid (CEVd); Hop stunt viroid (HSVd); and Citrus leprosis virus (CiLV). In some embodiments, the methods and kits additionally comprise components for detecting a housekeeping citrus gene, NADH dehydrogenase gene (Nad5) as an internal control.

In some aspects, the invention provides the following illustrative embodiments:

EMBODIMENT 1

A method for detecting the presence of at least one citrus pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus in a plant sample, the method comprising:
extracting RNA from said sample;
performing a multiplex branched DNA signal amplification reaction; wherein the reaction comprises at least one capture extender probe and at least one label extender probe that targets the pathogen, wherein the at least one capture extender probe and the at least one label extender probe each comprises at least 8, 9, or 10 contiguous nucleotide of a probe sequence shown in Table 1; and
detecting the presence or absence of a signal above background, wherein the presence of the signal is indicative of the presence of the pathogen.

EMBODIMENT 2

The method of embodiment 1, wherein the reaction comprises multiple capture extender probes and multiple label extender probes that target the pathogen, wherein each of the multiple capture extender probes and multiple label extender probes that target the pathogen comprises at least 8, 9, or 10 contiguous nucleotides of a probe sequence as shown in Table 1.

EMBODIMENT 3

The method of embodiment 1 or 2, wherein each of the probes that target the pathogen comprises a probe sequence set forth in Table 1.

EMBODIMENT 4

The method of embodiment 1, further comprising detecting the presence or absence of a second pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus in the plant sample, wherein the reaction comprises at least one capture extender probe and at least one label extender probe that target the second pathogen, wherein the capture extender probe and the label extender probe that target the second pathogen each comprise at least 8, 9, or 10 contiguous nucleotides of a probe sequence as shown in Table 1.

EMBODIMENT 5

The method of embodiment 4, wherein the reaction comprises multiple capture extender probes and multiple label extender probes that target the second pathogen, wherein each of the multiple capture extender probes and multiple label extender probes that target the second pathogen comprise at least 8, 9, or 10 contiguous nucleotides of a probe sequence as shown in Table 1.

EMBODIMENT 6

The method of embodiment 4 or 5, wherein each of the probes that target the second pathogen comprises a probe sequence as shown in Table 1.

EMBODIMENT 7

The method of embodiment 4, further comprising detecting the presence or absence of a third, fourth, fifth, sixth, seventh, or eighth pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus in the plant sample, wherein the reaction comprises at least one capture extender probe and at least one label extender probe that target the third, fourth, fifth, sixth, seventh, or eighth pathogen, wherein the capture extender probe and the label extender probe each comprise at least 8, 9, or 10 contiguous nucleotides of a probe sequence as shown in Table 1.

EMBODIMENT 8

The method of embodiment 7, wherein the reaction comprises multiple capture extender probes and multiple label extender probes that target the third, fourth, fifth, sixth, seventh, or eighth pathogen, wherein each of the multiple probes comprises at least 8, 9, or 10 contiguous nucleotides of a probe sequence as shown in Table 1.

EMBODIMENT 9

The method of embodiment 7 or 8, wherein each of the probes that target the third, fourth, fifth, sixth, seventh, or eighth pathogen comprises a probe sequence as shown in Table 1.

EMBODIMENT 10

The method of embodiment 1, comprising detecting the presence or absence of the nine pathogens Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, and Citrus leprosis virus in the plant sample, wherein for each of the nine pathogens, the reaction comprises a capture extender probe and a label extender probe, wherein each capture extender probe and each label extender probe comprises at least 8, 9, or 10 contiguous nucleotides of a probe sequence as shown in Table 1.

EMBODIMENT 11

The method of embodiment 10, wherein the reaction comprises multiple capture extender probes and multiple label extender probes that target each of the nine pathogens, wherein each of the multiple capture extender probes and each of the multiple label extender probes comprises at least 8, 9, or 10 contiguous nucleotides of a probe sequence shown in Table 1.

EMBODIMENT 12

The method of embodiment 10 or 11, wherein each of the probes that target the nine pathogens comprises a probe sequence shown in Table 1.

EMBODIMENT 13

The method of any one of embodiments 1 to 12, wherein the reaction comprises at least one blocking probe listed in Table 1 for the corresponding pathogen.

EMBODIMENT 14

The method of any one of embodiment 1 to 12, wherein the reaction comprises all of the blocking probes listed in Table 1.

EMBODIMENT 15

The method of any one of embodiments 1 to 14, wherein the reaction further comprises using one of the capture extender probes and one of the label extender probes for Nad5 listed in Table 1.

EMBODIMENT 16

The method of embodiment 15, wherein the reaction comprises using all of the label extender probes and all of the capture extender probes for Nad5 listed in Table 1.

EMBODIMENT 17

The method of any one of embodiments 1 to 16, wherein the plant sample is from seed, foliage, limbs, trunk, bark, rootstock, fruit, germplasm, propagule, cuttings, or budwood.

EMBODIMENT 18

A reaction mixture for detecting the presence of at least one citrus pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus in a plant sample, wherein the reaction mixture comprises at least one capture extender probe and at least one label extender probe that target the pathogen, where the at least one capture extender probe and at least one label extender probe comprises 8, 9, or 10 contiguous nucleotide of a probe sequence as shown in Table 1.

EMBODIMENT 19

The reaction mixture of embodiment 18, wherein the reaction comprises multiple capture extender probes and multiple label extender probes that target the pathogen, wherein each of the multiple capture extender probes and multiple label extender probes comprises at least 8, 9, or 10 contiguous nucleotides of a probe sequence as shown in Table 1.

EMBODIMENT 20

The reaction mixture of embodiment 18 or 19, wherein each of the probes that target the pathogen comprises a probe sequence set forth in Table 1.

EMBODIMENT 21

The reaction mixture of embodiment 18, further comprising at least one capture extender probe and at least one label extender probe that target a second pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus, wherein the capture extender probe and the label extender probe that target the second pathogen each comprise at least 8, 9, or 10 contiguous nucleotides of a probe sequence as shown in Table 1.

EMBODIMENT 22

The reaction mixture of embodiment 21, wherein the reaction comprises multiple capture extender probes and multiple label extender probes that target the second pathogen, wherein each of the multiple capture extender probes and multiple label extender probes comprises at least 8, 9, or 10 contiguous nucleotides of a probe sequence as shown in Table 1.

EMBODIMENT 23

The reaction mixture of embodiment 21 or 22, wherein each of the probes that target the second pathogen comprises a probe sequence as shown in Table 1.

EMBODIMENT 24

The reaction mixture of embodiment 21, further comprising at least one capture extender probe and at least one label extender probe that target a third, fourth, fifth, sixth, seventh, or eighth pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus, wherein the capture extender probe and the label extender probe each comprise at least 8, 9, or 10 contiguous nucleotides of a probe sequence as shown in Table 1.

EMBODIMENT 25

The reaction mixture of embodiment 24, wherein the reaction comprises multiple capture extender probes and multiple label extender probes that target the third, fourth, fifth, sixth, seventh, or eighth pathogen, wherein each of the multiple probes comprises at least 8, 9, or 10 contiguous nucleotides of a probe sequence as shown in Table 1.

EMBODIMENT 26

The reaction mixture of embodiment 24 or 25, wherein each of the probes that target the third, fourth, fifth, sixth, seventh, or eighth pathogen comprises a probe sequence as shown in Table 1.

EMBODIMENT 27

The reaction mixture of embodiment 18, comprising a capture extender probe and a label extender probe for each of the nine pathogens Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, and Citrus leprosis virus, wherein each capture extender probe and each label extender probe comprises at least 8, 9, or 10 contiguous nucleotides of a probe sequence as shown in Table 1.

EMBODIMENT 28

The reaction mixture of embodiment 27, comprising multiple capture extender probes and multiple label extender probes that target each of the nine pathogens, wherein each of the multiple capture extender probes and each of the multiple label extender probes comprises at least 8, 9, or 10 contiguous nucleotides of a probe sequence shown in Table 1.

EMBODIMENT 29

The reaction mixture of embodiment 27 or 28, wherein each of the probes that target the nine pathogens comprises a probe sequence shown in Table 1.

EMBODIMENT 30

The reaction mixture of any one of embodiments 18 to 29, wherein the reaction comprises at least one blocking probe listed in Table 1 for the corresponding pathogen.

EMBODIMENT 31

The reaction mixture of any one of embodiments 18 to 29, wherein the reaction mixture comprises all of the blocking probes listed in Table 1.

EMBODIMENT 32

The reaction mixture of any one of embodiments 18 to 31, wherein the reaction mixture further comprises one of the capture extender probes and one of the label extender probes for Nad5 listed in Table 1, or all of the capture extender probes and all of the label extender probes for Nad5 listed in Table 1.

EMBODIMENT 33

A kit mixture for detecting the presence of at least one citrus pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus in a plant sample, wherein the kit comprises at least one capture extender probe and at least one label extender probe that target the pathogen, where the at least one capture extender probe and at least one label extender probe comprises 8, 9, or 10 contiguous nucleotide of a probe sequence as shown in Table 1.

EMBODIMENT 34

The kit of embodiment 33, wherein the kit comprises multiple capture extender probes and multiple label extender probes that target the pathogen, wherein each of the multiple capture extender probes and multiple label extender probes comprises at least 8, 9, or 10 contiguous nucleotides of a probe sequence as shown in Table 1.

EMBODIMENT 35

The kit of embodiment 33 or 34, wherein each of the probes that target the pathogen comprises a probe sequence set forth in Table 1.

EMBODIMENT 36

The kit of embodiment 33, further comprising at least one capture extender probe and at least one label extender probe that target a second pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus, wherein the capture extender probe and the label extender probe that target the second pathogen each comprise at least 8, 9, or 10 contiguous nucleotides of a probe sequence as shown in Table 1.

EMBODIMENT 37

The kit of embodiment 36, wherein the reaction comprises multiple capture extender probes and multiple label extender probes that target the second pathogen, wherein each of the multiple capture extender probes and multiple label extender probes comprises at least 8, 9, or 10 contiguous nucleotides of a probe sequence as shown in Table 1.

EMBODIMENT 38

The kit of embodiment 36 or 37, wherein each of the probes that target the second pathogen comprises a probe sequence as shown in Table 1.

EMBODIMENT 39

The kit of embodiment 36, further comprising at least one capture extender probe and at least one label extender probe that target a third, fourth, fifth, sixth, seventh, or eighth pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus, wherein the capture extender probe and the label extender probe each comprise at least 8, 9, or 10 contiguous nucleotides of a probe sequence as shown in Table 1.

EMBODIMENT 40

The kit of embodiment 39, wherein the kit comprises multiple capture extender probes and multiple label extender probes that target the third, fourth, fifth, sixth, seventh, or eighth pathogen, wherein each of the multiple probes comprises at least 8, 9, or 10 contiguous nucleotides of a probe sequence as shown in Table 1.

EMBODIMENT 41

The kit of embodiment 39 or 40, wherein each of the probes that target the third, fourth, fifth, sixth, seventh, or eighth pathogen comprises a probe sequence as shown in Table 1.

EMBODIMENT 42

The kit of embodiment 33, comprising a capture extender probe and a label extender probe for each of the nine pathogens Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, and Citrus leprosis virus, wherein each capture extender probe and each label extender probe comprises at least 8, 9, or 10 contiguous nucleotides of a probe sequence as shown in Table 1.

EMBODIMENT 43

The kit of embodiment 42, comprising multiple capture extender probes and multiple label extender probes that target each of the nine pathogens, wherein each of the multiple capture extender probes and each of the multiple label extender probes comprises at least 8, 9, or 10 contiguous nucleotides of a probe sequence shown in Table 1.

EMBODIMENT 44

The kit of embodiment 42 or 43, wherein each of the probes that target the nine pathogens comprises a probe sequence shown in Table 1.

EMBODIMENT 45

The kit of any one of embodiments 33 to 44, wherein the kit comprises at least one blocking probe listed in Table 1 for the corresponding pathogen.

EMBODIMENT 46

The kit of any one of embodiments 33 to 44, wherein the kit comprises all of the blocking probes listed in Table 1.

EMBODIMENT 47

The kit of any one of embodiments 33 to 46, wherein the kit further comprises one of the capture extender probes and one of the label extender probes for Nad5 listed in Table 1, or all of the capture extender probes and all of the label extender probes for Nad5 listed in Table 1.

DETAILED DESCRIPTION OF THE INVENTION

Figure 1:
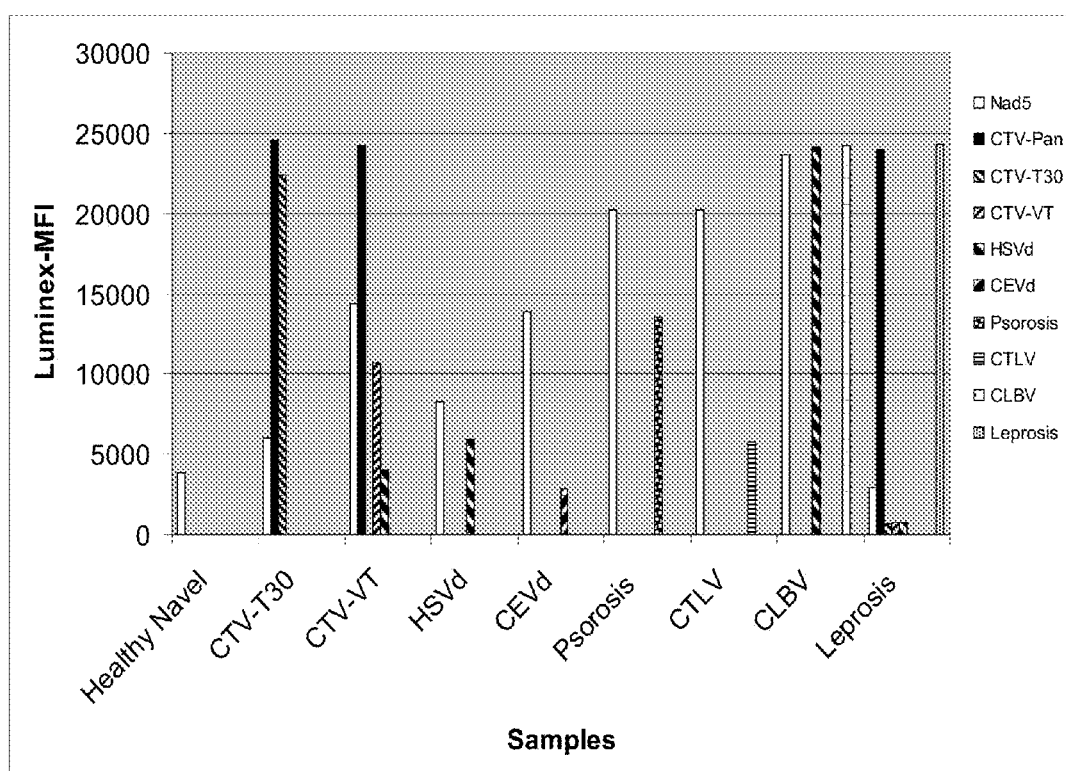
FIG. 1 provides illustrative data showing a 10-Plex reaction detecting citrus pathogens.

As used herein, a "probe that targets a pathogen" refers to a nucleotide sequence that hybridizes to a desired region of a target nucleic acid in the pathogen.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch. Typically, the total number of mismatched nucleotides over a hybridizing region is not more than 3 nucleotides for sequences about 15 nucleotides in length.

The term "probe" refers to an oligonucleotide that selectively hybridizes to a target nucleic acid under suitable conditions. A hybridization assay carried out using a probe under sufficiently stringent hybridization conditions enables the selective detection of a specific target sequence comprising the region of interest of a pathogen nucleic acid. The probe hybridizing region is preferably from about 10 to about 35 nucleotides in length. In some embodiments, the probe hybridizing region is 15 to about 35 nucleotides in length. The use of modified bases or base analogues which affect the hybridization stability, which are well known in the art, may enable the use of shorter or longer probes with comparable stability.

The term "target sequence" or "target region" refers to a region of a nucleic acid in a pathogen of interest to which a probe to the pathogen binds.

A "capture extender probe" or "CE probe" as used here is a polynucleotide that is capable of hybridizing to a nucleic acid of interest from a citrus pathogen and to a capture probe. The capture extender probe has a first polynucleotide sequence that is complementary to a capture probe, and a second polynucleotide sequence, e.g., a sequence as shown in Table 1, which is complementary to a citrus pathogen nucleic acid as described herein. The capture probe is typically immobilized to a solid support, including but not limited to a chip (e.g., an array), well, bead, or other solid support or matrix.

A "label extender probe" or "LE" as used here is a polynucleotide that is capable of hybridizing to a nucleic acid of interest from a pathogen and to a label probe system. The label extender probe has a first polynucleotide sequence that is complementary to a polynucleotide sequence of the label probe system and a second polynucleotide sequence, e.g., a sequence as shown in Table 1, which is complementary to a citrus pathogen as described herein. The signal-amplifying probe in the present invention typically comprises branched DNA, e.g., may include a pre-Amplifier probe, an Amplifier probe, and a Label probe.

Introduction

The present invention provides methods to diagnose infection with citrus pathogens. In some embodiments, the methods can be used in high-throughput screenings of thousands of plant samples in regulatory and research programs. Branched DNA technology (bDNA) employs a sandwich nucleic acid hybridization assay for nucleic acid detection and quantification that amplifies the reporter signal rather than the target sequence of interest that is to be detected. Thus, bDNA technology amplifies signal directly from captured target RNA without purification or reverse transcription. RNA quantitation is performed directly from a tissue sample. By measuring the nucleic acid at the sample source, the assay avoids variations or errors inherent to extraction and amplification of target polynucleotides. The QuantiGene Plex technology can be combined with multiplex bead based assay system such as the Luminex system described below to enable simultaneous detection of multiple pathogens of interest.

In brief, in an assay of the invention, a target nucleic acid to be detected is released from cells and captured by a Capture Probe (CP) on a solid surface (e.g., a well of a microtiter plate) through synthetic oligonucleotide probes called Capture Extenders (CEs). Each capture extender has a first polynucleotide sequence that can hybridize to the target nucleic acid and a second polynucleotide sequence that can hybridize to the capture probe. Typically, two or more capture extenders are used. Probes of another type, called Label Extenders (LEs), hybridize to different sequences on the target nucleic acid and to sequences on an amplification multimer. Additionally, Blocking Probes (BPs), which hybridize to regions of the target nucleic acid not occupied by CEs or LEs, are typically used to reduce non-specific target probe binding. A probe set for a given nucleic acid thus has CEs, LEs, and typically BPs for the target citrus pathogen. The CEs, LEs, and BPs are complementary to nonoverlapping sequences in the target nucleic acid from the citrus pathogen, and are typically, but not necessarily, contiguous.

Signal amplification begins with the binding of the LEs to the target mRNA. An amplification multimer is then typically hybridized to the LEs. The amplification multimer has multiple copies of a sequence that is complementary to a label probe (it is worth noting that the amplification multimer is typically, but not necessarily, a branched-chain nucleic acid; for example, the amplification multimer can be a branched, forked, or comb-like nucleic acid or a linear nucleic acid). A label, for example, alkaline phosphatase, is covalently attached to each label probe. (Alternatively, the label can be noncovalently bound to the label probes.) In the final step, labeled complexes are detected, e.g., by the alkaline phosphatase-mediated degradation of a chemiluminegenic substrate, e.g., dioxetane. Luminescence is reported as relative light unit (RLUs) on a microplate reader. The amount of chemiluminescence is proportional to the level of mRNA expressed from the target gene.

The present invention provides a method and compositions for detecting the presence or absence of at least one, at least two, at least three, at least four, at least five, at least six, at least seven, at least eight, or all nine of the citrus pathogens described herein. As explained above, detection is performed using bDNA signal amplification technology and capture extender probes and label extender probes that target the pathogen nucleic acid regions described herein. The general design of branched amplification assays, e.g., suitable amplification multimers, considerations in designing capture probes that bind to the capture extenders, etc.; configuration; and hybridization conditions for such reactions can be determined using methods known in the art (see, e.g., U.S. Patent Application Publication No. 20120003648 and the references cited therein).

Citrus Pathogen Probes

The nine pathogen targets and internal citrus gene were developed based on specific genomic sequences and characteristics in the pathogens' genome. The probes (Table 1) included Capture Extenders (CE), Label Extenders (LE), Blocking Probes (BL) as per manufacturer's recommendations were designed and developed based on the conserved sequences in the genome of each pathogen. CTV-Pan (universal) probes was designed based on the pathogen sequence alignment of CTV isolates worldwide and included all major CTV genotypes. CTV-T30 (mild strain) probes were designed based on the sequence alignment of worldwide T30 genotype isolates. CTV-VT probes were designed based on sequence alignment of worldwide CTV isolates having a VT genotype. Similarly, probes for CPV, CTLV, CLBV, CEVd, HSVd and CiLV were based on pathogen sequence alignment from data deposited in GenBank. In the present invention, the CE and LE probe sequences shown in Table 1 are the regions of the CE and LE oligonucleotides that target the pathogen.

The present invention employs CE and LE probes that comprise sequences presented in Table 1 or are variants of the sequences in Table 1 that retain the ability to hybridize to the same target nucleic acid sequence as the probes shown in Table 1 such that the presence of the pathogen in a plant sample can be detected. Such variant probe sequences typically have no more than 1, 2, 3, 4, 5, 6, 7, or 8 nucleotide changes relative to a probe sequence as shown in Table 1. In some embodiments, a variant probe useful in the invention comprises at least 7, 8, 9, 10, 11, 12, 13, 14, 15, 16, 17, 18, 19, or 20, or more, contiguous nucleotides of a sequence shown in Table 1.

The methods and compositions for detecting one or more of the 9 citrus pathogens as described herein may also include probe to detect a control nucleic acid sequence. In some embodiments, the control is a housekeeping gene that is common to citrus plants. In some embodiments, the housekeeping gene is NADH dehydrogenase gene. In some embodiments, the CE and LE probes comprises the NAD sequences shown in Table 1 or are variants of the sequences that retain the ability to hybridize to the target region in the NAD sequence. In some embodiments, such a variant probe comprises at least 7, 8, 9, 10, 11, 12, 13, 14, 15, 16, 17, 18, 19, or 20, or more, contiguous nucleotides of a sequence shown in Table 1; or has no more than 1, 2, 3, 4, 5, 6, 7, or 8 nucleotide changes relative to the sequence shown in Table 1.

In some embodiments, one or more blocking probes may be employed. Table 1 provides examples of sequences that may be employed in blocking probes useful in the invention.

In some embodiments, multiple capture extender and/or label extender probes shown in Table 1, or variants thereof as described herein, are used in the invention. In some embodiments, each of the probes that target a pathogen is shown in Table 1. In some embodiments, all of the probes, including any blocking probes, shown in Table 1, or variants thereof as described herein, for a given pathogen are used in the invention.

Plant Samples

The sample evaluated for the presence of citrus pathogens can be from any plant material (e.g., seed, foliage, limbs, trunk, bark, rootstock, fruit, germplasm, propagule, cuttings, and budwood). RNA is extracted using well known techniques. Such an RNA sample may also comprise DNA. Methods for extracting RNA from a plant samples are known to those skilled in the art and are described in Bilgin et al., *Nature Protocols*, 4:333-340, (2009); Berendzen et al., *Plant Methods*, 1:4 (2005); Elspeth MacRae, *Methods in Molecular Biology*, vol. 353: *Protocols for Nucleic Acid Analysis by Nonradioactive Probes, Second Edition*, Humana Press, New Jersey, 15-24, (2007). Non-limiting examples of commercially available plant RNA extraction kits include include RNAeasy Plant Mini Kit (Qiagen, Hilden, Germany), PrepEase Plant Spin Kit (Affymetrix, Santa Clara, Calif.), Agilent Plant RNA Isolation Mini Kit (Agilent Technologies, Santa Clara, Calif.), Plant RNA Isolation Aid (Ambion, Austin, Tex.), and Spectrum Plant total RNA kit (Sigma-Aldrich, St. Louis, Mo.).

The following examples are offered to illustrate, but not to limit, the claimed invention.

EXAMPLES

Example 1. High Throughput Assays for Rapid and Accurate 10-Plex Detection of Citrus Pathogens The assay was developed using a QuantiGene Plex and Luminex based assay procedure. The probes used for detecting the pathogens are shown in Table 1.

TABLE 1

Sequence of specific probes including Capture Extenders (CE), Label Extenders (LE), Blocking Probes (BL) designed and developed for the specific detection of nine citrus pathogen targets and a housekeeping citrus gene as an internal control with QuantiGene Plex and Luminex based assay.

| Targets $^a$ | Probes | Probe sequence (5'→3') | SEQ ID NO: |
|---|---|---|---|
| CTV-Pan (all | CTV001 CE | ctccgcctgaaacactcagactc | 1 |
| | CTV002 CE | atgaagtggtgttcacggagaa | 2 |
| | CTV003 CE | attttaaagactttacccatccggt | 3 |
| major CTV genotypes) | CTV004 CE | ggttcacgcatacgttaagcc | 4 |
| | CTV005 CE | aacacacactctaaggagaacttcttt | 5 |
| | CTV006 CE | cccccatagggacagtgtgttgg | 6 |
| | CTV007 LE | gaacttattccgtccacttcaatcag | 7 |
| | CTV008 LE | aagggtttttaccaacccgacata | 8 |
| | CTV009 LE | tattgtctagtgatacatcaccatcat | 9 |
| | CTV010 LE | atatggttaattttccctcgatc | 10 |
| | CTV011 LE | gggagcttagaccaacgagagg | 11 |
| | CTV012 LE | tcacttgagaccactaccactctgt | 12 |
| CTV-T30 (CTV-T30 genotype) | T30001 CE | cgggtgaatttgaatcgaaatt | 13 |
| | T30002 CE | ggatcgagctccggagata | 14 |
| | T30003 CE | ccaagtcccgcagggtcc | 15 |
| | T30004 CE | aaccgtctggttgggatttaca | 16 |
| | T30005 CE | tgtattgatattatgggcgtagaac | 17 |
| | T30006 CE | aagggacgatcggcccagcagcc | 18 |
| | T30007 CE | catacctccaagcgcccgcaa | 19 |
| | T30008 CE | tggggactttcacgcacagt | 20 |
| | T30009 LE | agcgaaagtcgaggacttgaa | 21 |
| | T30010 LE | cgaaattatgtaatcgctgcgtac | 22 |
| | T30011 LE | aggcgcgccagatgcg | 23 |
| | T30012 LE | tgcaggactccaacggtattaa | 24 |
| | T30013 LE | ggttgtatcagtgccgaagaag | 25 |
| | T30014 LE | gaaaactccttaaccaccgtagt | 26 |
| | T30015 LE | ttaatcgcgcgaacagca | 27 |
| | T30016 LE | aataggacgtccggcagct | 28 |
| | T30017 LE | cggagcgcggagcgtc | 29 |
| | T30018 LE | ggaggccacagaggcatc | 30 |
| | T30019 LE | acaccagatgtgtcgaaaacag | 31 |
| | T30020 LE | cagagcggggacgcacg | 32 |
| | T30023 LE | tcttcgccttgcgaatgga | 33 |
| | T30024 LE | ggctgagaaagaatgcagaatctt | 34 |
| | T30025 LE | cgagagaagagagaagaagccc | 35 |
| | T30026 LE | gtgccgcaagggacttcc | 36 |
| | T30027 LE | gcctgcgaagtctgtgacgc | 37 |
| | T30028 LE | agggtcaactagtttcgcaacac | 38 |
| | T30029 BL | gctagctccgagtttcgacatat | 39 |
| | T30031 BL | gcgcgaactgagaacgga | 40 |
| CTV-VT (CTV-VT genotype) | VT002 CE | ggacgtgatttccggaggg | 41 |
| | VT003 CE | accgattcccgcagcgt | 42 |
| | VT004 CE | ggcaatttgccgggatttac | 43 |
| | VT005 CE | atttgtttgtatgggcgtagtg | 44 |
| | VT007 CE | agaatacctccaaatgcccg | 45 |
| | VT008 CE | ggcgtcccttaagtttgatct | 46 |
| | VT009 LE | gaaagtcaaggacttgaagcg | 47 |
| | VT010 LE | tgatgtaatcgctgcgtacagc | 48 |
| | VT011 LE | gcgccagatgcgcgaga | 49 |
| | VT012 LE | gactccaacggtgttaaaggc | 50 |
| | VT013 LE | ggttgtttcagtaccgaagaagt | 51 |
| | VT014 LE | aaaattccttaaccaccttggt | 52 |
| | VT015 LE | ttaatcgcgcgaacagca | 53 |
| | VT016 LE | tgggacgtccggcagct | 54 |
| | VT017 LE | agagcgcggagcgtcaa | 55 |
| | VT018 LE | ggaggccacagaggcatcc | 56 |
| | VT019 LE | cgacaccagatgtgtcgataacag | 57 |
| | VT020 LE | cgacagagcgggggacgta | 58 |
| | VT021 LE | gcagtaagggggaggtttacacag | 59 |
| | VT022 LE | tggacttcttggcggcg | 60 |
| | VT023 LE | tctttcttcgccttgcgaa | 61 |
| | VT024 LE | ccggctaagaagaaagaaagcagaa | 62 |
| | VT025 LE | cgtgccgcaggggactt | 63 |
| | VT026 LE | gcgcctacgaagtctatgacg | 64 |
| | VT027 LE | atggtagggtctactcgtttcataac | 65 |
| | VT028 LE | cgtcttggggactctcgtgc | 66 |
| | VT029 BL | agctccgagtttcgacatgttat | 67 |

TABLE 1-continued

Sequence of specific probes including Capture Extenders (CE), Label Extenders (LE), Blocking Probes (BL) designed and developed for the specific detection of nine citrus pathogen targets and a housekeeping citrus gene as an internal control with QuantiGene Plex and Luminex based assay.

| Targets [a] | Probes | Probe sequence (5'→3') | SEQ ID NO: |
|---|---|---|---|
|  | VT030 BL | aaacaggatttccgtagaggg | 68 |
|  | VT031 BL | gcgcgaacagaaaacgga | 69 |
|  | VT032 BL | cccgtgagaagagtgaagaagc | 70 |
| Psorosis (CPsV) | psoro001 CE | tggcgatggtgaagggcc | 71 |
|  | psoro002 CE | aagaacaaggggtttcagaatgatag | 72 |
|  | psoro003 CE | agcctcactccagatggcaga | 73 |
|  | psoro004 CE | tcaattgcaataagagattttctgaa | 74 |
|  | psoro005 CE | ctcctgaatccctgatgccatt | 75 |
|  | psoro006 CE | atctgtgagatatgctgggtttgc | 76 |
|  | psoro007 CE | aacaaagaaattccctgcaaggg | 77 |
|  | psoro008 CE | gtgaggaattgagccatgctcc | 78 |
|  | psoro009 LE | catggagtgtgttgacaaaacca | 79 |
|  | psoro010 LE | attgacatggccgagaggataataa | 80 |
|  | psoro011 LE | aaaaggcttcatcctttatctgatga | 81 |
|  | psoro012 LE | tggagggacaatggaagaatcag | 82 |
|  | psoro013 LE | gctggaaaccaatcaaaagattgaaaaa | 83 |
|  | psoro014 LE | gtccctgctgttggtgcaa | 84 |
|  | psoro015 LE | tgtttctcaagattgatatagacaactt | 85 |
|  | psoro016 LE | gaagctgtatgatggtgatgtaagttt | 86 |
| CTLV | CTLV001 CE | tgctgagagggacctaaatcctct | 87 |
|  | CTLV002 CE | gggaggaaccgtcagaagttcc | 88 |
|  | CTLV003 CE | gtgattgcagagaagaaggtaaagctc | 89 |
|  | CTLV004 CE | aagaaattcacgagccaaatcagc | 90 |
|  | CTLV005 CE | caaaagctttgggccatttct | 91 |
|  | CTLV006 CE | cctgcctcgaaaacccctttt | 92 |
|  | CTLV007 LE | tgttgaagcacgtcttccaaactcat | 93 |
|  | CTLV008 LE | gaaactgggtcttatcagatgaccc | 94 |
|  | CTLV009 LE | agaagtagcagcaaaaggttttcaattc | 95 |
|  | CTLV010 LE | ttgtccttcagtacgaaaaagcct | 96 |
|  | CTLV011 LE | cgactcctaaccctccagttcca | 97 |
|  | CTLV012 LE | cctgcaagaccgcgaccaa | 98 |
|  | CTLV013 LE | ttaagtataaaggcaggcatgtcaa | 99 |
| CLBV | CLBV001 CE | cagctctgaattttcgaatgatgtca | 100 |
|  | CLBV002 CE | ttgagtgactcattcaattcttcaa | 101 |
|  | CLBV003 CE | cccagccaaaattgcagct | 102 |
|  | CLBV004 CE | atctttgggaaatgtctttcaact | 103 |
|  | CLBV005 CE | gctcatgcccttttttttttcaaatt | 104 |
|  | CLBV006 LE | tgaggaatggttcaactatggct | 105 |
|  | CLBV007 LE | tcagaatttctgtcctcatcagatg | 106 |
|  | CLBV008 LE | tctccatgctcggccacta | 107 |
|  | CLBV009 LE | tcagggtccacctcctctgtg | 108 |
|  | CLBV010 LE | tgtgatctcaagctgtgatgcat | 109 |
|  | CLBV011 LE | ttcaagctgctgctctctatctgc | 110 |
|  | CLBV012 LE | ccactgccggtcagtggtt | 111 |
|  | CLBV013 LE | cagcatgtaccggttcagaagat | 112 |
|  | CLBV014 LE | actgtggagcgtgtgctgatt | 113 |
|  | CLBV015 LE | gcagatcattcaccacatgca | 114 |
|  | CLBV016 BL | ggaaaaaatggcgaagaagacc | 115 |
|  | CLBV017 BL | cttttttttgaataaactctgccgtac | 116 |
|  | CLBV018 BL | tgtttctcagatcttctgcttctgc | 117 |
| CEVd | CEVd001 CE | tcttttttcttttcctgcctgc | 118 |
|  | CEVd002 CE | ggatccctgaaggacttctt | 119 |
|  | CEVd003 CE | tcctccaggtttcccggg | 120 |
|  | CEVd004 CE | ttctccgctggacgccag | 121 |
|  | CEVd005 CE | cctcgcccggagagcagt | 122 |
|  | CEVd006 CE | tagggttccgagggctttcac | 123 |
|  | CEVd007 LE | ggaacctcaagaaagatcccg | 124 |
|  | CEVd008 LE | agggtcaggtgagcaccaca | 125 |
|  | CEVd009 LE | cccccgacctcgact | 126 |
|  | CEVd010 LE | tgatccgcggcgaccg | 127 |
|  | CEVd011 LE | aaaggaaggagacgagctcctgt | 128 |
|  | CEVd012 LE | ggatgtggagccagcagcg | 129 |
|  | CEVd013 LE | tcagttgtttccaccgggtagt | 130 |
|  | CEVd014 LE | gcggtttggggttgaagct | 131 |
| HSVd | CVdll001 CE | ttttctttgcttgcccatgc | 132 |
|  | CVdll002 CE | ggattctgagaagagttgcccc | 133 |
|  | CVdll003 CE | agctagaagcctctactccagagc | 134 |
|  | CVdll004 CE | ggacgatcgatggtgtttcga | 135 |
|  | CVdll005 CE | agccaggagggaaaggtaaaagaagaag | 136 |
|  | CVdll006 CE | cgaaccgagaggtgatgcca | 137 |
|  | CVdll007 LE | ggcaactcgagaattcccag | 138 |
|  | CVdll008 LE | ggggctcctttctcaggtaagt | 139 |
|  | CVdll009 LE | accgcgggccctctctcc | 140 |
|  | CVdll010 LE | ccggtcgcgtctcatcgga | 141 |
|  | CVdll011 LE | ggcagaggctcagatagacaaaaa | 142 |
|  | CVdll012 LE | gggctcaagagaggatccgc | 143 |
| Leprosis (CiLV) | leprosis3\| CE | tgctaatatcacgcagaccttca | 144 |
|  | leprosis9\| CE | ggccttctgcttagcaggttt | 145 |
|  | leprosis11\| CE | tgggtggagcaagctgctt | 146 |
|  | leprosis14\| CE | cggcatattttgggcagtg | 147 |
|  | leprosis18\| CE | gcttccattacccttaaaatcaggta | 148 |
|  | leprosis19\| CE | gacggcaactaggtcctcagaa | 149 |
|  | leprosis1\| LE | ctcaatggcctgcataatctca | 150 |
|  | leprosis2\| LE | ggaacagacacgttgtgccg | 151 |
|  | leprosis4\| LE | actgctgcttcttcttagtaggct | 152 |
|  | leprosis5\| LE | gtgacagttgttgaggttgcg | 153 |
|  | leprosis7\| LE | ccggggttgcagttgctgag | 154 |
|  | leprosis8\| LE | cttggcctgataaccactagga | 155 |
|  | leprosis16\| LE | ttataatatgtcatccctatctgcttc | 156 |
|  | leprosis17\| LE | acgcatagggctcggatatc | 157 |
|  | leprosis21\| LE | atactatataagcgcttctcaaagct | 158 |
|  | leprosis22\| LE | gtcgcttcgggaagccc | 159 |
|  | leprosis23\| LE | ccgggacaacgttctttatgg | 160 |
|  | leprosis24\| LE | caatgtagtgatcactgaactcgaata | 161 |
| Nad5 | Nad54\|CE | ggtcattatagcggttccttctga | 162 |
|  | Nad55\|CE | gaagagaatgaaacgcacgtagt | 163 |
|  | Nad59\|CE | caaacatttccgatgagatcca | 164 |
|  | Nad515\|CE | aataacacataaatcgagggctatg | 165 |
|  | Nad519\|CE | aaatatgaagcaagacctactccct | 166 |
|  | Nad522\|CE | ctcgattgacaggcatagcttct | 167 |
|  | Nad51\|LE | gggcaaaaatacgataagtagataca | 168 |
|  | Nad52\|LE | ctgctacggaactaccgagaag | 169 |
|  | Nad56\|LE | tcataaaaagcaatcagagataagatc | 170 |
|  | Nad57\|LE | actagctcccggtgcgact | 171 |
|  | Nad510\|LE | caagaagcccaagaagcat | 172 |
|  | Nad511\|LE | actacggtcgggctatcgaa | 173 |
|  | Nad512\|LE | cttatggatgtaaccacaattaacatc | 174 |
|  | Nad513\|LE | tggaataaagatggaccaagcta | 175 |
|  | Nad517\|LE | gagagttatctccagtcaccaat | 176 |
|  | Nad518\|LE | cccatcccaggaataattgaa | 177 |

TABLE 1-continued

Sequence of specific probes including Capture
Extenders (CE), Label Extenders (LE), Blocking
Probes (BL) designed and developed for the
specific detection of nine citrus pathogen
targets and a housekeeping citrus gene as an
internal control with QuantiGene Plex and
Luminex based assay.

| Targets [a] | Probes | Probe sequence (5'→3') | SEQ ID NO: |
|---|---|---|---|
| | Nad520\|LE | gtcgtgtaaaccagaaatgaattaac | 178 |
| | Nad521\|LE | tgtagctgctttatctgcctgaa | 179 |

[a] CTV-Pan: Citrus tristeza virus major genotypes (universal), CTV-T30: CTV genotype T30, CTV-VT: CTV genotype VT, Psorosis: Citrus psorosis virus (CPsV), CTLV: Citrus tatter leaf virus, CLBV: Citrus leaf blotch virus, CEVd: Citrus exocortis viroid, HSVd: Hop stunt viroid (syn. citrus viroid IIa, IIb, and IIc), Leprosis: Citrus leprosis virus (CiLV), Nad5: NADH dehydrogenase gene, a housekeeping citrus gene, used as an internal control.

The procedure from the QuantiGene Plex 2.0 Assay User Manual from Affymetrix/Panomics Inc is shown below:

Capturing Target RNA from Total, Purified, In Vitro Transcribed RNA or Total Nucleic Acid 1. Sample and reagent preparation: thaw probe set, blocking reagent and total nucleic acid samples (both RNA and DNA or RNA only), and place them on ice.
2. Pre-warm lysis mixture at 37° C. for 30 minutes.
3. Prepare a working bead mix including nuclease-free water, lysis mixture, blocking reagent, capture beads, probe set, according to reaction composition (Table 2).

TABLE 2

Working Bead Mix Set Up

| Order of addition | Reagent | Per well (µl) |
|---|---|---|
| 1 | Nuclease-free water | 38.7 |
| 2 | Lysis mixture | 33.3 |
| 3 | Blocking reagent | 2 |
| 4 | Capture beads | 1 |
| 5 | Probe set | 5 |
| | Total | 80 |

4. Vortex working bead mix for 30 sec, transfer 80 µl to each well of the hybridization plate.
5. Add 20 µl nucleic acid samples (or RNA sample) to each well of the above plate.
6. Seal the hybridization plate with a pressure seal and mount the plate into the shaking incubator.
7. Incubate for 18-22 hours at 54° C. at 600 rpm.

Signal Amplification and Detection of RNA Targets

1. Place label probe diluent and SAPE diluent to room temperature. Incubate amplifier diluent at 37° C. for 20 minutes.
2. Prepare 200 ml wash buffer including 0.6 ml wash buffer Component 1, 10 ml wash buffer Component 2 and 189.4 ml nuclease-free water.
3. Add 36 µl pre-amplifier to 12 ml amplifier diluent.
4. Take the hybridization plate out of the shaking incubator, and spin at 240 g for 60 seconds.
5. Open the pressure seal, mix with pipette, then transfer the hybridization mixture to the magnetic separation plate.
6. Put the magnetic separation plate on the plate holder of the plate washer for 60 seconds, then empty the magnetic separation plate and wash three times with 100 µl wash buffer.
7. Add 100 µl pre-amplifier solution to each well.
8. Seal the magnetic separation plate with a foil plate seal and shake for 60 minutes at 50° C. with 600 rpm.
9. Add 36 µl amplifier to 12 ml amplifier diluent.
10. Take the magnetic separation plate out of the shaking incubator.
11. Open the foil plate seal.
12. Put the magnetic separation plate on the plate holder of the plate washer for 60 seconds, then empty the magnetic separation plate and wash three times with 100 µl wash buffer.
13. Add 100 µl amplifier solution to each well.
14. Seal the magnetic separation plate with a foil plate seal and shake for 60 minutes at 50° C. with 600 rpm.
15. Add 36 µl label probe to 12 ml label probe diluent.
16. Take the magnetic separation plate out of the shaking incubator and open the foil plate seal.
17. Put the magnetic separation plate on the plate holder of the plate washer for 60 seconds, then empty the magnetic separation plate and wash three times with 100 µl wash buffer.
18. Add 100 µl label probe solution to each well.
19. Seal the magnetic separation plate with a foil plate seal and shake for 60 minutes at 50° C. with 600 rpm.
20. Add 36 µl SAPE to 12 ml SAPE diluent.
21. Take the magnetic separation plate out of the shaking incubator and open the foil plate seal.
22. Put the magnetic separation plate on the plate holder of the plate washer for 60 seconds, then empty the magnetic separation plate and wash three times with 100 µl wash buffer.
23. Add 100 µl SAPE solution to each well.
24. Seal the magnetic separation plate with a foil plate seal and shake for 30 minutes at 50° C. with 600 rpm.
25. Take the magnetic separation plate out of the shaking incubator, open the foil plate seal.
26. Put the magnetic separation plate on the plate holder of the plate washer for 60 seconds, then empty the magnetic separation plate and wash three times with 100 µl SAPE wash buffer.
27. Add 130 µl SAPE wash buffer to each well.
28. Seal the magnetic separation plate with a foil plate seal and cover the magnetic separation plate with foil and shake for 2-3 minutes at room temperature with 600 rpm, then use Luminex instrument to read.

Initially, the assay was performed using nine samples from healthy and infected citrus plants with CTV genotype T30, CTV genotype VT, CPsV (Psorosis), CTLV, CLBV, CEVd, HSVd, CiLV (Leprosis), respectively (FIG. 1). A procedure for high throughput robotic extraction and purification of nucleic acid targets, optimized for citrus tissues, was developed and used with the Luminex-based QuantiGene Plex system to increase uniformity and cost effectiveness of the test. Sample CTV-T30 was detected to show positive reactions with both CTV-Pan and CTV-T30, but not CTV-VT and other pathogen targets. In addition, sample CTV-T30 was detected to show positive reactions with Nad5, the positive internal control for citrus plants, which could be used to access the RNA extraction quality and to normalize data for accurate quantification of the pathogen populations among samples. Sample CTV-VT was confirmed to have CTV genotype VT and HSVd from other studies. In contrast to sample CTV-T30, CTV-VT was detected to show positive reactions with Nad5, CTV-Pan, CTV-VT, and HSVd, but not CTV-T30 and the other RNA pathogen targets. Sample HSVd showed positive reactions with Nad5 and HSVd, but not other pathogen targets.

Similarly, samples CEVd, CPsV and CTLV showed positive reactions with Nad5 and their pathogen targets, respectively, but not other pathogen targets. Sample CLBV was confirmed to have HSVd and CLBV from other studies. In the assay, sample CLBV showed positive reactions with Nad5, CLBV and HSVd, but not other pathogen targets. Sample Leprosis was confirmed to have CTV, HSVd and Psorosis from other studies. In the assay, sample Leprosis showed positive reactions with Leprosis, Nad5, CTV-Pan, CTV-T30, CTV-VT, and HSVd. Finally, the healthy Navel sweet orange control sample showed positive reaction with Nad5 but not to any pathogen targets. These data showed that the assay is capable of specific detection of each target including Nad5, CTV-Pan, CTV genotype T30, CTV genotype VT, Psorosis, CTLV, CLBV, CEVd, HSVd, and Leprosis.

Figure 2:
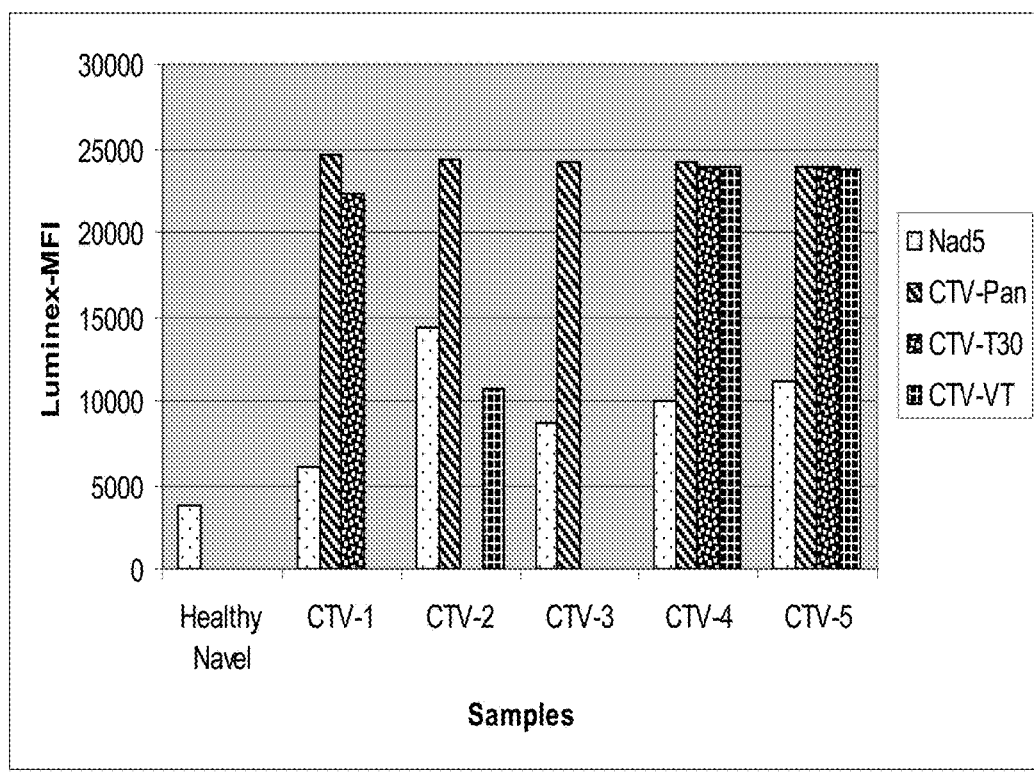
FIG. 2 provides illustrative data showing universal and genotype-specific detection of citrus pathogen CTV.

Developmental assays were performed using more CTV samples from healthy and infected citrus plants (FIG. 2). Every sample tested had a positive reaction with Nad5 indicating that nucleic acid extracted per plant was effective. In addition, sample CTV-1 containing CTV genotype T30 showed positive reactions with both CTV-Pan and CTV-T30, but not CTV-VT. Sample CTV-2 containing CTV genotype VT showed positive reactions with both CTV-Pan and CTV-VT, but not CTV-T30. Sample CTV-3 containing CTV genotype T36 showed positive reaction with CTV-Pan only, but not to CTV-T30 or CTV-VT. Lastly, samples 4 and 5 containing both T30 and VT genotypes showed positive reactions with CTV-Pan, CTV-T30 and CTV-VT. These data further validate the 10-plex detection system could detect broad-spectrum CTV strains but also the major genotypes T30 and VT.

Figure 3:
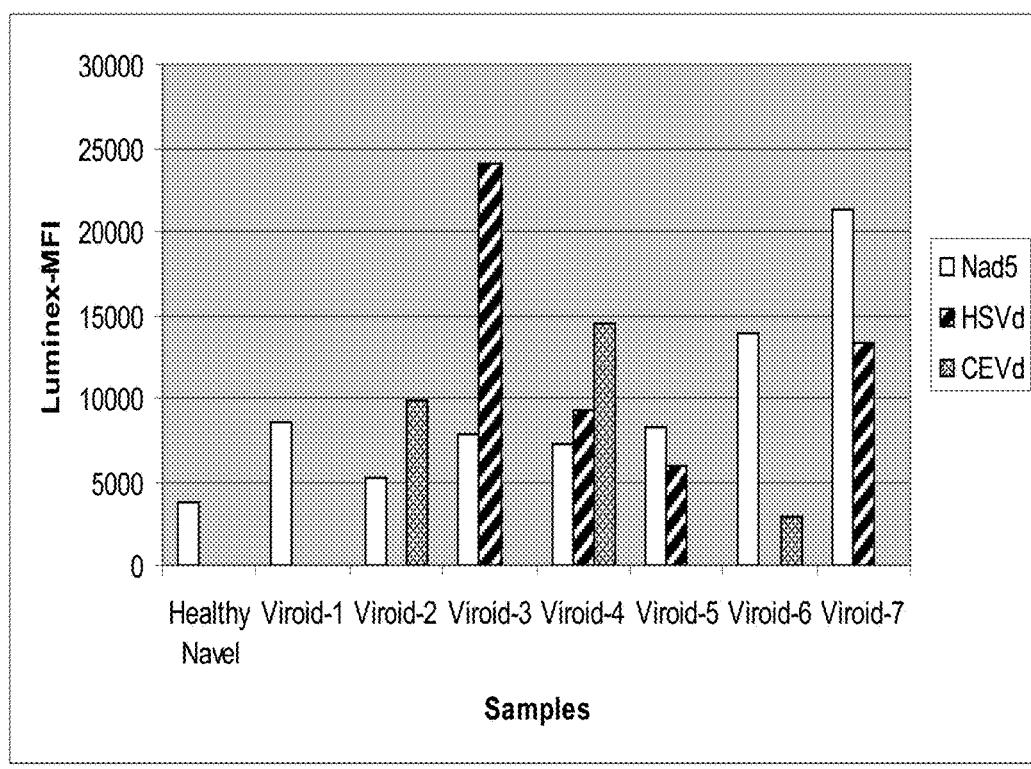
FIG. 3 provides illustrative data showing specific detection of citrus viroids CEVd and HSVd.

The assay was also performed using healthy citrus and citrus infected with citrus viroids (FIG. 3). There are seven known distinct viroid species representing four genera in the Pospiviroidae family. They are: Citrus exocortis viroid (CEVd, genus Pospiviroid), Hop stunt viroid (HSVd, genus Hostuviroid), Citrus bark cracking viroid (CBCVd, genus Cocadviroid) and Citrus bent leaf viroid (CBLVd), Citrus dwarfing viroid (CDVd), Citrus viroid V (CVd-V) and CVd-VI of the genus Apscaviroid. Collectively, these various citrus viroids cause abnormal growth. All samples tested were positive for Nad5 and demonstrated good quality nucleic acid extraction and purification. Viroid-3, -5 and -7 contained HSVd and showed positive reaction with HSVd but not CEVd. Viroid-6 contained CEVd and showed a positive reaction with CEVd but not HSVd. Samples infected with known multiple viroid species were also tested in the assay. Sample viroid-2 contained CEVd and CBCVd and showed a positive reaction with CEVd, but not HSVd. Sample viroid-4 containing CBLVd, HSVd, CDVd, CBCVd, CVd-V and CEVd showed positive reactions with both CEVd and HSVd. In short, it was further validated that the 10-plex detection system could detect specifically different citrus viroid species CEVd and HSVd, respectively.

The high throughput robotic extraction and purification of nucleic acid targets, optimized for citrus tissues, it showed that samples obtained from fresh or frozen tissue crude extraction using QuantiGene sample processing kit were consistently detected. Finally, sensitivity studies using serial dilutions of CTV and HSVd samples, respectively, suggested that those samples, obtained by the high throughput robotic extraction and purification of nucleic acid targets, were consistently detected after dilution of up to 1000 times.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A reaction mixture comprising probes (a) for detecting the presence of two or more citrus pathogens selected from the group consisting of Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, and Citrus leprosis virus, wherein the reaction mixture comprises at least one capture extender probe and at least one label extender probe for targeting each of the two or more pathogens selected from a set of detection probes as follows:

a capture extender probe that targets CTV universal and comprises at least 8, 9, or 10 contiguous nucleotides of a probe sequence of SEQ ID NO:1, 2, 3, 4, 5, or 6; and a label extender probe that targets CTV universal and comprises at least 8, 9, or 10 contiguous nucleotides of a probe sequence of SEQ ID NO: 7, 8, 9, 10, 11, or 12;

a capture extender probe that targets CTV genotype T30 and comprises at least 8, 9, or 10 contiguous nucleotides of a probe sequence of SEQ ID NO:13, 14, 15, 16, 17, 18, 19, or 20; and a label extender probe that targets CTV genotype T30 and comprises at least 8, 9, or 10 contiguous nucleotides of a probe sequence of SEQ ID NO:21, 22, 23, 24, 25, 26, 27, 28, 29, 30, 31, 32, 33, 34, 35, 36, 37, or 38;

a capture extender probe that targets CTV VT genotype and comprises at least 8, 9, or 10 contiguous nucleotides of a probe sequence of SEQ ID NO:41, 42, 43, 44, 45, or 46; and a label extender probe that targets CTV VT genotype and comprises at least 8, 9, or 10 contiguous nucleotides of a probe sequence of SEQ ID NO:47, 48, 49, 50, 51, 52, 53, 54, 55, 56, 57, 58, 59, 60, 61, 62, 63, 64, 65, or 66;

a capture extender probe that targets Citrus psorosis virus and comprises at least 8, 9, or 10 contiguous nucleotides of a probe sequence of SEQ ID NO:71, 72, 73, 74, 75, 76, 77, or 78; and a label extender probe that targets Citrus psorosis virus and comprises at least 8, 9, or 10 contiguous nucleotides of a probe sequence of SEQ ID NO:79, 80, 81, 82, 83, 84, 85, or 86;

a capture extender probe that targets Citrus tatter leaf virus and comprises at least 8, 9, or 10 contiguous nucleotides of a probe sequence of SEQ ID NO:87, 88, 89, 90, 91, or 92; and a label extender probe that targets Citrus tatter leaf virus and comprises at least 8, 9, or 10 contiguous nucleotides of a probe sequence of SEQ ID NO:93, 94, 95, 96, 97, 98, or 99;

a capture extender probe that targets Citrus leaf blotch virus and comprises at least 8, 9, or 10 contiguous nucleotides of a probe sequence of SEQ ID NO:100, 101, 102, 103, or 104; and a label extender probe that targets Citrus leaf blotch virus and comprises at least 8, 9, or 10 contiguous nucleotides of a probe sequence of SEQ ID NO:105, 106, 107, 108, 109, 110, 111, 112, 113, or 114:

a capture extender probe that targets Citrus exocortis virus and comprises at least 8, 9, or 10 contiguous nucleotides of a probe sequence of SEQ ID NO:118, 119, 120, 121, 122, or 123; and a label extender probe that targets Citrus exocortis virus and comprises at least 8, 9, or 10 contiguous nucleotides of a probe sequence of SEQ ID NO:124, 125, 126, 127, 128, 129, 130, or 131;

a capture extender probe that targets Hop stunt viroid and comprises at least 8, 9, or 10 contiguous nucleotides of a probe sequence of SEQ ID NO:133, 134, 135, 136, or 137; and a label extender probe that targets Hop stunt viroid and comprises at least 8, 9, or 10 contiguous nucleotides of a probe sequence of SEQ ID NO:138, 139, 140, 141, 142, or 143; and a capture extender probe that targets Citrus leprosis virus and comprises at least 8, 9, or 10 contiguous nucleotides of a probe sequence of SEQ ID NO:144, 145, 146, 147, 148, or 149; and a label extender probe that targets Citrus leprosis virus comprises at least 8, 9, or 10 contiguous nucleotides of a probe sequence of SEQ ID NO:150, 151, 152, 153, 154, 155, 156, 157, 158, 159, 160, or 161, further, wherein the capture extender probe comprises a sequence that hybridizes to a capture probe immobilized on a solid support; and (b) a capture probe that hybridizes to one or more of capture extender probes.

2. The reaction mixture of claim 1, wherein the reaction comprises multiple capture extender probes and multiple label extender probes that target the pathogen.

3. The reaction mixture of claim 1, further comprising at least one capture extender probe and at least one label extender probe that target a third, fourth, fifth, sixth, seventh, or eighth pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus.

4. The reaction mixture of claim 3, wherein the reaction comprises multiple capture extender probes and multiple label extender probes that target the third, fourth, fifth, sixth, seventh, or eighth pathogen.

5. The reaction mixture of claim 1, comprising a capture extender probe and a label extender probe for each of the nine pathogens Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, and Citrus leprosis virus.

6. The reaction mixture of claim 5, comprising multiple capture extender probes and multiple label extender probes that target each of the nine pathogens.

7. A kit for detecting the presence of two or more citrus pathogens selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus in a plant sample, wherein the kit comprises (a) at least one capture extender probe and at least one label extender probe that target each of the two or more pathogens, wherein the at least one capture extender probe and at least one label extender probe for targeting each of the two or more pathogens is selected from a set of detection probes as follows:

a capture extender probe that targets CTV universal and comprises at least 8, 9, or 10 contiguous nucleotides of a probe sequence of SEQ ID NO:1, 2, 3, 4, 5, or 6; and a label extender probe that targets CTV universal and comprises at least 8, 9, or 10 contiguous nucleotides of a probe sequence of SEQ ID NO: 7, 8, 9, 10, 11, or 12;

a capture extender probe that targets CTV genotype T30 and comprises at least 8, 9, or 10 contiguous nucleotides of a probe sequence of SEQ ID NO:13, 14, 15, 16, 17, 18, 19, or 20; and a label extender probe that targets CTV genotype T30 and comprises at least 8, 9, or 10 contiguous nucleotides of a probe sequence of SEQ ID NO:21, 22, 23, 24, 25, 26, 27, 28, 29, 30, 31, 32, 33, 34, 35, 36, 37, or 38;

a capture extender probe that targets CTV VT genotype and comprises at least 8, 9, or 10 contiguous nucleotides of a probe sequence of SEQ ID NO:41, 42, 43, 44, 45, or 46; and a label extender probe that targets CTV VT genotype and comprises at least 8, 9, or 10 contiguous nucleotides of a probe sequence of SEQ ID NO:47, 48, 49, 50, 51, 52, 53, 54, 55, 56, 57, 58, 59, 60, 61, 62, 63, 64, 65, or 66;

a capture extender probe that targets Citrus psorosis virus and comprises at least 8, 9, or 10 contiguous nucleotides of a probe sequence of SEQ ID NO:71, 72, 73, 74, 75, 76, 77, or 78; and a label extender probe that targets Citrus psorosis virus and comprises at least 8, 9, or 10 contiguous nucleotides of a probe sequence of SEQ ID NO:79, 80, 81, 82, 83, 84, 85, or 86;

a capture extender probe that targets Citrus tatter leaf virus and comprises at least 8, 9, or 10 contiguous nucleotides of a probe sequence of SEQ ID NO:87, 88, 89, 90, 91, or 92; and a label extender probe that targets Citrus tatter leaf virus and comprises at least 8, 9, or 10 contiguous nucleotides of a probe sequence of SEQ ID NO:93, 94, 95, 96, 97, 98, or 99;

a capture extender probe that targets Citrus leaf blotch virus and comprises at least 8, 9, or 10 contiguous nucleotides of a probe sequence of SEQ ID NO:100, 101, 102, 103, or 104; and a label extender probe that targets Citrus leaf blotch virus and comprises at least 8, 9, or 10 contiguous nucleotides of a probe sequence of SEQ ID NO:105, 106, 107, 108, 109, 110, 111, 112, 113, or 114:

a capture extender probe that targets Citrus exocortis virus and comprises at least 8, 9, or 10 contiguous nucleotides of a probe sequence of SEQ ID NO:118, 119, 120, 121, 122, or 123; and a label extender probe that targets Citrus exocortis virus and comprises at least 8, 9, or 10 contiguous nucleotides of a probe sequence of SEQ ID NO:124, 125, 126, 127, 128, 129, 130, or 131;

a capture extender probe that targets Hop stunt viroid and comprises at least 8, 9, or 10 contiguous nucleotides of a probe sequence of SEQ ID NO:133, 134, 135, 136, or 137; and a label extender probe that targets Hop stunt viroid and comprises at least 8, 9, or 10 contiguous nucleotides of a probe sequence of SEQ ID NO:138, 139, 140, 141, 142, or 143; and a capture extender probe that targets Citrus leprosis virus and comprises at least 8, 9, or 10 contiguous nucleotides of a probe sequence of SEQ ID NO:144, 145, 146, 147, 148, or 149; and a label extender probe that targets Citrus leprosis virus comprises at least 8, 9, or 10 contiguous nucleotides of a probe sequence of SEQ ID NO:150, 151, 152, 153, 154, 155, 156, 157, 158, 159, 160, or 161, further, wherein the capture extender probe comprises a sequence that hybridizes to a capture probe immobilized on a solid support; and (b) a capture probe that hybridizes to one or more of capture extender probes.

8. The kit of claim 7, wherein the kit comprises multiple capture extender probes and multiple label extender probes that target the two or more pathogens.

9. The kit of claim 7, further comprising at least one capture extender probe and at least one label extender probe that target a third, fourth, fifth, sixth, seventh, or eighth pathogen selected from Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, or Citrus leprosis virus.

10. The kit of claim 9, wherein the kit comprises multiple capture extender probes and multiple label extender probes that target the third, fourth, fifth, sixth, seventh, or eighth pathogen.

11. The kit of claim 7, comprising a capture extender probe and a label extender probe for each of the nine pathogens Citrus tristeza virus (CTV) universal, CTV genotype T30, CTV genotype VT, Citrus psorosis virus, Citrus tatter leaf virus, Citrus leaf blotch virus, Citrus exocortis viroid, Hop stunt viroid, and Citrus leprosis virus.

12. The kit of claim 11, comprising multiple capture extender probes and multiple label extender probes that target each of the nine pathogens.

* * * * *

SEQUENCE LISTING

```
<160> NUMBER OF SEQ ID NOS: 179

<210> SEQ ID NO 1
<211> LENGTH: 23
<212> TYPE: DNA
<213> ORGANISM: Artificial Sequence
<220> FEATURE:
<223> OTHER INFORMATION: synthetic CTV001 Capture Extender (CE) probe
      for detection of all major genotypes of citrus pathogen
      Citrus tristeza virus (CTV), CTV-Pan target

<400> SEQUENCE: 1
ctccgcctga aacactcaga ctc                                            23

<210> SEQ ID NO 2
<211> LENGTH: 22
<212> TYPE: DNA
<213> ORGANISM: Artificial Sequence
<220> FEATURE:
<223> OTHER INFORMATION: synthetic CTV002 Capture Extender (CE) probe
      for detection of all major genotypes of citrus pathogen
      Citrus tristeza virus (CTV), CTV-Pan target

<400> SEQUENCE: 2
atgaagtggt gttcacggag aa                                             22
```

```
<210> SEQ ID NO 3
<211> LENGTH: 25
<212> TYPE: DNA
<213> ORGANISM: Artificial Sequence
<220> FEATURE:
<223> OTHER INFORMATION: synthetic CTV003 Capture Extender (CE) probe
      for detection of all major genotypes of citrus pathogen
      Citrus tristeza virus (CTV), CTV-Pan target

<400> SEQUENCE: 3
attttaaaga ctttacccat ccggt                                              25

<210> SEQ ID NO 4
<211> LENGTH: 21
<212> TYPE: DNA
<213> ORGANISM: Artificial Sequence
<220> FEATURE:
<223> OTHER INFORMATION: synthetic CTV004 Capture Extender (CE) probe
      for detection of all major genotypes of citrus pathogen
      Citrus tristeza virus (CTV), CTV-Pan target

<400> SEQUENCE: 4
ggttcacgca tacgttaagc c                                                  21

<210> SEQ ID NO 5
<211> LENGTH: 27
<212> TYPE: DNA
<213> ORGANISM: Artificial Sequence
<220> FEATURE:
<223> OTHER INFORMATION: synthetic CTV005 Capture Extender (CE) probe
      for detection of all major genotypes of citrus pathogen
      Citrus tristeza virus (CTV), CTV-Pan target

<400> SEQUENCE: 5
aacacacact ctaaggagaa cttctttt                                           27

<210> SEQ ID NO 6
<211> LENGTH: 23
<212> TYPE: DNA
<213> ORGANISM: Artificial Sequence
<220> FEATURE:
<223> OTHER INFORMATION: synthetic CTV006 Capture Extender (CE) probe
      for detection of all major genotypes of citrus pathogen
      Citrus tristeza virus (CTV), CTV-Pan target

<400> SEQUENCE: 6
cccccatagg gacagtgtgt tgg                                                23

<210> SEQ ID NO 7
<211> LENGTH: 26
<212> TYPE: DNA
<213> ORGANISM: Artificial Sequence
<220> FEATURE:
<223> OTHER INFORMATION: synthetic CTV007 Label Extender (LE) probe for
      detection of all major genotypes of citrus
      pathogen Citrus tristeza virus (CTV), CTV-Pan
      target

<400> SEQUENCE: 7
gaacttattc cgtccacttc aatcag                                             26

<210> SEQ ID NO 8
<211> LENGTH: 24
<212> TYPE: DNA
<213> ORGANISM: Artificial Sequence
<220> FEATURE:
<223> OTHER INFORMATION: synthetic CTV008 Label Extender (LE) probe for
      detection of all major genotypes of citrus pathogen
      Citrus tristeza virus (CTV), CTV-Pan target
```

<400> SEQUENCE: 8
aagggttttt accaacccga cata                                                                    24

<210> SEQ ID NO 9
<211> LENGTH: 27
<212> TYPE: DNA
<213> ORGANISM: Artificial Sequence
<220> FEATURE:
<223> OTHER INFORMATION: synthetic CTV009 Label Extender (LE) probe for
      detection of all major genotypes of citrus pathogen
      Citrus tristeza virus (CTV), CTV-Pan target

<400> SEQUENCE: 9
tattgtctag tgatacatca ccatcat                                                                 27

<210> SEQ ID NO 10
<211> LENGTH: 24
<212> TYPE: DNA
<213> ORGANISM: Artificial Sequence
<220> FEATURE:
<223> OTHER INFORMATION: synthetic CTV010 Label Extender (LE) probe for
      detection of all major genotypes of citrus pathogen
      Citrus tristeza virus (CTV), CTV-Pan target

<400> SEQUENCE: 10
atatggttaa ttttcccctc gatc                                                                    24

<210> SEQ ID NO 11
<211> LENGTH: 22
<212> TYPE: DNA
<213> ORGANISM: Artificial Sequence
<220> FEATURE:
<223> OTHER INFORMATION: synthetic CTV011 Label Extender (LE) probe for
      detection of all major genotypes of citrus pathogen
      Citrus tristeza virus (CTV), CTV-Pan target

<400> SEQUENCE: 11
gggagcttag accaacgaga gg                                                                      22

<210> SEQ ID NO 12
<211> LENGTH: 25
<212> TYPE: DNA
<213> ORGANISM: Artificial Sequence
<220> FEATURE:
<223> OTHER INFORMATION: synthetic CTV012 Label Extender (LE) probe for
      detection of all major genotypes of citrus pathogen
      Citrus tristeza virus (CTV), CTV-Pan target

<400> SEQUENCE: 12
tcacttgaga ccactaccac tctgt                                                                   25

<210> SEQ ID NO 13
<211> LENGTH: 22
<212> TYPE: DNA
<213> ORGANISM: Artificial Sequence
<220> FEATURE:
<223> OTHER INFORMATION: synthetic T30001 Capture Extender (CE) probe
      for detection of T30 genotypes of citrus pathogen
      Citrus tristeza virus (CTV), CTV-T30 target

<400> SEQUENCE: 13
cgggtgaatt tgaatcgaaa tt                                                                      22

<210> SEQ ID NO 14
<211> LENGTH: 19
<212> TYPE: DNA

```
<213> ORGANISM: Artificial Sequence
<220> FEATURE:
<223> OTHER INFORMATION: synthetic T30002 Capture Extender (CE) probe
      for detection of T30 genotypes of citrus pathogen
      Citrus tristeza virus (CTV), CTV-T30 target

<400> SEQUENCE: 14
ggatcgagct ccggagata                                                    19

<210> SEQ ID NO 15
<211> LENGTH: 18
<212> TYPE: DNA
<213> ORGANISM: Artificial Sequence
<220> FEATURE:
<223> OTHER INFORMATION: synthetic T30003 Capture Extender (CE) probe
      for detection of T30 genotypes of citrus pathogen
      Citrus tristeza virus (CTV), CTV-T30 target

<400> SEQUENCE: 15
ccaagtcccg cagggtcc                                                     18

<210> SEQ ID NO 16
<211> LENGTH: 22
<212> TYPE: DNA
<213> ORGANISM: Artificial Sequence
<220> FEATURE:
<223> OTHER INFORMATION: synthetic T30004 Capture Extender (CE) probe
      for detection of T30 genotypes of citrus pathogen
      Citrus tristeza virus (CTV), CTV-T30 target

<400> SEQUENCE: 16
aaccgtctgg ttgggattta ca                                                22

<210> SEQ ID NO 17
<211> LENGTH: 25
<212> TYPE: DNA
<213> ORGANISM: Artificial Sequence
<220> FEATURE:
<223> OTHER INFORMATION: synthetic T30005 Capture Extender (CE) probe
      for detection of T30 genotypes of citrus pathogen
      Citrus tristeza virus (CTV), CTV-T30 target

<400> SEQUENCE: 17
tgtattgata ttatgggcgt agaac                                             25

<210> SEQ ID NO 18
<211> LENGTH: 23
<212> TYPE: DNA
<213> ORGANISM: Artificial Sequence
<220> FEATURE:
<223> OTHER INFORMATION: synthetic T30006 Capture Extender (CE) probe
      for detection of T30 genotypes of citrus pathogen
      Citrus tristeza virus (CTV), CTV-T30 target

<400> SEQUENCE: 18
aagggacgat cggcccagca gcc                                               23

<210> SEQ ID NO 19
<211> LENGTH: 21
<212> TYPE: DNA
<213> ORGANISM: Artificial Sequence
<220> FEATURE:
<223> OTHER INFORMATION: synthetic T30007 Capture Extender (CE) probe
      for detection of T30 genotypes of citrus pathogen
      Citrus tristeza virus (CTV), CTV-T30 target

<400> SEQUENCE: 19
catacctcca agcgcccgca a                                                 21
```

```
<210> SEQ ID NO 20
<211> LENGTH: 20
<212> TYPE: DNA
<213> ORGANISM: Artificial Sequence
<220> FEATURE:
<223> OTHER INFORMATION: synthetic T30008 Capture Extender (CE) probe
      for detection of T30 genotypes of citrus pathogen
      Citrus tristeza virus (CTV), CTV-T30 target

<400> SEQUENCE: 20
tggggacttt cacgcacagt                                              20

<210> SEQ ID NO 21
<211> LENGTH: 21
<212> TYPE: DNA
<213> ORGANISM: Artificial Sequence
<220> FEATURE:
<223> OTHER INFORMATION: synthetic T30009 Label Extender (LE) probe for
      detection of T30 genotypes of citrus pathogen
      Citrus tristeza virus (CTV), CTV-T30 target

<400> SEQUENCE: 21
agcgaaagtc gaggacttga a                                            21

<210> SEQ ID NO 22
<211> LENGTH: 24
<212> TYPE: DNA
<213> ORGANISM: Artificial Sequence
<220> FEATURE:
<223> OTHER INFORMATION: synthetic T30010 Label Extender (LE) probe for
      detection of T30 genotypes of citrus pathogen
      Citrus tristeza virus (CTV), CTV-T30 target

<400> SEQUENCE: 22
cgaaattatg taatcgctgc gtac                                         24

<210> SEQ ID NO 23
<211> LENGTH: 16
<212> TYPE: DNA
<213> ORGANISM: Artificial Sequence
<220> FEATURE:
<223> OTHER INFORMATION: synthetic T30011 Label Extender (LE) probe for
      detection of T30 genotypes of citrus pathogen
      Citrus tristeza virus (CTV), CTV-T30 target

<400> SEQUENCE: 23
aggcgcgcca gatgcg                                                  16

<210> SEQ ID NO 24
<211> LENGTH: 22
<212> TYPE: DNA
<213> ORGANISM: Artificial Sequence
<220> FEATURE:
<223> OTHER INFORMATION: synthetic T30012 Label Extender (LE) probe for
      detection of T30 genotypes of citrus pathogen
      Citrus tristeza virus (CTV), CTV-T30 target

<400> SEQUENCE: 24
tgcaggactc caacggtatt aa                                           22

<210> SEQ ID NO 25
<211> LENGTH: 22
<212> TYPE: DNA
<213> ORGANISM: Artificial Sequence
<220> FEATURE:
<223> OTHER INFORMATION: synthetic T30013 Label Extender (LE) probe for
      detection of T30 genotypes of citrus pathogen
```

Citrus tristeza virus (CTV), CTV-T30 target

<400> SEQUENCE: 25
ggttgtatca gtgccgaaga ag                                    22

<210> SEQ ID NO 26
<211> LENGTH: 23
<212> TYPE: DNA
<213> ORGANISM: Artificial Sequence
<220> FEATURE:
<223> OTHER INFORMATION: synthetic T30014 Label Extender (LE) probe for
      detection of T30 genotypes of citrus pathogen
      Citrus tristeza virus (CTV), CTV-T30 target

<400> SEQUENCE: 26
gaaaactcct taaccaccgt agt                                   23

<210> SEQ ID NO 27
<211> LENGTH: 18
<212> TYPE: DNA
<213> ORGANISM: Artificial Sequence
<220> FEATURE:
<223> OTHER INFORMATION: synthetic T30015 Label Extender (LE) probe for
      detection of T30 genotypes of citrus pathogen
      Citrus tristeza virus (CTV), CTV-T30 target

<400> SEQUENCE: 27
ttaatcgcgc gaacagca                                         18

<210> SEQ ID NO 28
<211> LENGTH: 19
<212> TYPE: DNA
<213> ORGANISM: Artificial Sequence
<220> FEATURE:
<223> OTHER INFORMATION: synthetic T30016 Label Extender (LE) probe for
      detection of T30 genotypes of citrus pathogen
      Citrus tristeza virus (CTV), CTV-T30 target

<400> SEQUENCE: 28
aataggacgt ccggcagct                                        19

<210> SEQ ID NO 29
<211> LENGTH: 16
<212> TYPE: DNA
<213> ORGANISM: Artificial Sequence
<220> FEATURE:
<223> OTHER INFORMATION: synthetic T30017 Label Extender (LE) probe for
      detection of T30 genotypes of citrus pathogen
      Citrus tristeza virus (CTV), CTV-T30 target

<400> SEQUENCE: 29
cggagcgcgg agcgtc                                           16

<210> SEQ ID NO 30
<211> LENGTH: 18
<212> TYPE: DNA
<213> ORGANISM: Artificial Sequence
<220> FEATURE:
<223> OTHER INFORMATION: synthetic T30018 Label Extender (LE) probe for
      detection of T30 genotypes of citrus pathogen
      Citrus tristeza virus (CTV), CTV-T30 target

<400> SEQUENCE: 30
ggaggccaca gaggcatc                                         18

<210> SEQ ID NO 31
<211> LENGTH: 22

```
<212> TYPE: DNA
<213> ORGANISM: Artificial Sequence
<220> FEATURE:
<223> OTHER INFORMATION: synthetic T30019 Label Extender (LE) probe for
      detection of T30 genotypes of citrus pathogen
      Citrus tristeza virus (CTV), CTV-T30 target

<400> SEQUENCE: 31
acaccagatg tgtcgaaaac ag                                              22

<210> SEQ ID NO 32
<211> LENGTH: 17
<212> TYPE: DNA
<213> ORGANISM: Artificial Sequence
<220> FEATURE:
<223> OTHER INFORMATION: synthetic T30020 Label Extender (LE) probe for
      detection of T30 genotypes of citrus pathogen
      Citrus tristeza virus (CTV), CTV-T30 target

<400> SEQUENCE: 32
cagagcgggg acgcacg                                                    17

<210> SEQ ID NO 33
<211> LENGTH: 19
<212> TYPE: DNA
<213> ORGANISM: Artificial Sequence
<220> FEATURE:
<223> OTHER INFORMATION: synthetic T30023 Label Extender (LE) probe for
      detection of T30 genotypes of citrus pathogen
      Citrus tristeza virus (CTV), CTV-T30 target

<400> SEQUENCE: 33
tcttcgcctt gcgaatgga                                                  19

<210> SEQ ID NO 34
<211> LENGTH: 24
<212> TYPE: DNA
<213> ORGANISM: Artificial Sequence
<220> FEATURE:
<223> OTHER INFORMATION: synthetic T30024 Label Extender (LE) probe for
      detection of T30 genotypes of citrus pathogen
      Citrus tristeza virus (CTV), CTV-T30 target

<400> SEQUENCE: 34
ggctgagaaa gaatgcagaa tctt                                            24

<210> SEQ ID NO 35
<211> LENGTH: 22
<212> TYPE: DNA
<213> ORGANISM: Artificial Sequence
<220> FEATURE:
<223> OTHER INFORMATION: synthetic T30025 Label Extender (LE) probe for
      detection of T30 genotypes of citrus pathogen
      Citrus tristeza virus (CTV), CTV-T30 target

<400> SEQUENCE: 35
cgagagaaga gagaagaagc cc                                              22

<210> SEQ ID NO 36
<211> LENGTH: 18
<212> TYPE: DNA
<213> ORGANISM: Artificial Sequence
<220> FEATURE:
<223> OTHER INFORMATION: synthetic T30026 Label Extender (LE) probe for
      detection of T30 genotypes of citrus pathogen
      Citrus tristeza virus (CTV), CTV-T30 target

<400> SEQUENCE: 36
```

```
gtgccgcaag ggacttcc                                                    18

<210> SEQ ID NO 37
<211> LENGTH: 20
<212> TYPE: DNA
<213> ORGANISM: Artificial Sequence
<220> FEATURE:
<223> OTHER INFORMATION: synthetic T30027 Label Extender (LE) probe for
      detection of T30 genotypes of citrus pathogen
      Citrus tristeza virus (CTV), CTV-T30 target

<400> SEQUENCE: 37
gcctgcgaag tctgtgacgc                                                  20

<210> SEQ ID NO 38
<211> LENGTH: 23
<212> TYPE: DNA
<213> ORGANISM: Artificial Sequence
<220> FEATURE:
<223> OTHER INFORMATION: synthetic T30028 Label Extender (LE) probe for
      detection of T30 genotypes of citrus pathogen
      Citrus tristeza virus (CTV), CTV-T30 target

<400> SEQUENCE: 38
agggtcaact agtttcgcaa cac                                              23

<210> SEQ ID NO 39
<211> LENGTH: 23
<212> TYPE: DNA
<213> ORGANISM: Artificial Sequence
<220> FEATURE:
<223> OTHER INFORMATION: synthetic T30029 Blocking Probe (BL) for
      detection of T30 genotypes of citrus pathogen Citrus
      tristeza virus (CTV), CTV-T30 target

<400> SEQUENCE: 39
gctagctccg agtttcgaca tat                                              23

<210> SEQ ID NO 40
<211> LENGTH: 18
<212> TYPE: DNA
<213> ORGANISM: Artificial Sequence
<220> FEATURE:
<223> OTHER INFORMATION: synthetic T30031 Blocking Probe (BL) for
      detection of T30 genotypes of citrus pathogen Citrus
      tristeza virus (CTV), CTV-T30 target

<400> SEQUENCE: 40
gcgcgaactg agaacgga                                                    18

<210> SEQ ID NO 41
<211> LENGTH: 19
<212> TYPE: DNA
<213> ORGANISM: Artificial Sequence
<220> FEATURE:
<223> OTHER INFORMATION: synthetic VT002 Capture Extender (CE) probe for
      detection of VT genotypes of citrus pathogen
      Citrus tristeza virus (CTV), CTV-VT target

<400> SEQUENCE: 41
ggacgtgatt tccggaggg                                                   19

<210> SEQ ID NO 42
<211> LENGTH: 17
<212> TYPE: DNA
<213> ORGANISM: Artificial Sequence
<220> FEATURE:
<223> OTHER INFORMATION: synthetic VT003 Capture Extender (CE) probe for
``` detection of VT genotypes of citrus pathogen
Citrus tristeza virus (CTV), CTV-VT target

<400> SEQUENCE: 42
accgattccc gcagcgt                                                    17

<210> SEQ ID NO 43
<211> LENGTH: 20
<212> TYPE: DNA
<213> ORGANISM: Artificial Sequence
<220> FEATURE:
<223> OTHER INFORMATION: synthetic VT004 Capture Extender (CE) probe for
      detection of VT genotypes of citrus pathogen
      Citrus tristeza virus (CTV), CTV-VT target

<400> SEQUENCE: 43
ggcaatttgc cgggatttac                                                 20

<210> SEQ ID NO 44
<211> LENGTH: 22
<212> TYPE: DNA
<213> ORGANISM: Artificial Sequence
<220> FEATURE:
<223> OTHER INFORMATION: synthetic VT005 Capture Extender (CE) probe for
      detection of VT genotypes of citrus pathogen
      Citrus tristeza virus (CTV), CTV-VT target

<400> SEQUENCE: 44
atttgtttgt atgggcgtag tg                                              22

<210> SEQ ID NO 45
<211> LENGTH: 20
<212> TYPE: DNA
<213> ORGANISM: Artificial Sequence
<220> FEATURE:
<223> OTHER INFORMATION: synthetic VT007 Capture Extender (CE) probe for
      detection of VT genotypes of citrus pathogen
      Citrus tristeza virus (CTV), CTV-VT target

<400> SEQUENCE: 45 agaataccctc caaatgcccg                                                20

<210> SEQ ID NO 46
<211> LENGTH: 21
<212> TYPE: DNA
<213> ORGANISM: Artificial Sequence
<220> FEATURE:
<223> OTHER INFORMATION: synthetic VT008 Capture Extender (CE) probe for
      detection of VT genotypes of citrus pathogen
      Citrus tristeza virus (CTV), CTV-VT target

<400> SEQUENCE: 46 ggcgtcccctt aagtttgatc t                                              21

<210> SEQ ID NO 47
<211> LENGTH: 21
<212> TYPE: DNA
<213> ORGANISM: Artificial Sequence
<220> FEATURE:
<223> OTHER INFORMATION: synthetic VT009 Label Extender (LE) probe for
      detection of VT genotypes of citrus pathogen
      Citrus tristeza virus (CTV), CTV-VT target

<400> SEQUENCE: 47
gaaagtcaag gacttgaagc g                                               21

<210> SEQ ID NO 48

<210> SEQ ID NO 48
<211> LENGTH: 22
<212> TYPE: DNA
<213> ORGANISM: Artificial Sequence
<220> FEATURE:
<223> OTHER INFORMATION: synthetic VT010 Label Extender (LE) probe for
    detection of VT genotypes of citrus pathogen
    Citrus tristeza virus (CTV), CTV-VT target

<400> SEQUENCE: 48
tgatgtaatc gctgcgtaca gc                                          22

<210> SEQ ID NO 49
<211> LENGTH: 17
<212> TYPE: DNA
<213> ORGANISM: Artificial Sequence
<220> FEATURE:
<223> OTHER INFORMATION: synthetic VT011 Label Extender (LE) probe for
    detection of VT genotypes of citrus pathogen
    Citrus tristeza virus (CTV), CTV-VT target

<400> SEQUENCE: 49
gcgccagatg cgcgaga                                                17

<210> SEQ ID NO 50
<211> LENGTH: 21
<212> TYPE: DNA
<213> ORGANISM: Artificial Sequence
<220> FEATURE:
<223> OTHER INFORMATION: synthetic VT012 Label Extender (LE) probe for
    detection of VT genotypes of citrus pathogen
    Citrus tristeza virus (CTV), CTV-VT target

<400> SEQUENCE: 50
gactccaacg gtgttaaagg c                                           21

<210> SEQ ID NO 51
<211> LENGTH: 23
<212> TYPE: DNA
<213> ORGANISM: Artificial Sequence
<220> FEATURE:
<223> OTHER INFORMATION: synthetic VT013 Label Extender (LE) probe for
    detection of VT genotypes of citrus pathogen
    Citrus tristeza virus (CTV), CTV-VT target

<400> SEQUENCE: 51
ggttgtttca gtaccgaaga agt                                         23

<210> SEQ ID NO 52
<211> LENGTH: 22
<212> TYPE: DNA
<213> ORGANISM: Artificial Sequence
<220> FEATURE:
<223> OTHER INFORMATION: synthetic VT014 Label Extender (LE) probe for
    detection of VT genotypes of citrus pathogen
    Citrus tristeza virus (CTV), CTV-VT target

<400> SEQUENCE: 52
aaaattcctt aaccaccttg gt                                          22

<210> SEQ ID NO 53
<211> LENGTH: 18
<212> TYPE: DNA
<213> ORGANISM: Artificial Sequence
<220> FEATURE:
<223> OTHER INFORMATION: synthetic VT015 Label Extender (LE) probe for
    detection of VT genotypes of citrus pathogen
    Citrus tristeza virus (CTV), CTV-VT target

<400> SEQUENCE: 53
ttaatcgcgc gaacagca                                                  18

<210> SEQ ID NO 54
<211> LENGTH: 17
<212> TYPE: DNA
<213> ORGANISM: Artificial Sequence
<220> FEATURE:
<223> OTHER INFORMATION: synthetic VT016 Label Extender (LE) probe for
      detection of VT genotypes of citrus pathogen
      Citrus tristeza virus (CTV), CTV-VT target

<400> SEQUENCE: 54
tgggacgtcc ggcagct                                                   17

<210> SEQ ID NO 55
<211> LENGTH: 17
<212> TYPE: DNA
<213> ORGANISM: Artificial Sequence
<220> FEATURE:
<223> OTHER INFORMATION: synthetic VT017 Label Extender (LE) probe for
      detection of VT genotypes of citrus pathogen
      Citrus tristeza virus (CTV), CTV-VT target

<400> SEQUENCE: 55
agagcgcgga gcgtcaa                                                   17

<210> SEQ ID NO 56
<211> LENGTH: 19
<212> TYPE: DNA
<213> ORGANISM: Artificial Sequence
<220> FEATURE:
<223> OTHER INFORMATION: synthetic VT018 Label Extender (LE) probe for
      detection of VT genotypes of citrus pathogen
      Citrus tristeza virus (CTV), CTV-VT target

<400> SEQUENCE: 56
ggaggccaca gaggcatcc                                                 19

<210> SEQ ID NO 57
<211> LENGTH: 24
<212> TYPE: DNA
<213> ORGANISM: Artificial Sequence
<220> FEATURE:
<223> OTHER INFORMATION: synthetic VT019 Label Extender (LE) probe for
      detection of VT genotypes of citrus pathogen
      Citrus tristeza virus (CTV), CTV-VT target

<400> SEQUENCE: 57
cgacaccaga tgtgtcgata acag                                           24

<210> SEQ ID NO 58
<211> LENGTH: 18
<212> TYPE: DNA
<213> ORGANISM: Artificial Sequence
<220> FEATURE:
<223> OTHER INFORMATION: synthetic VT020 Label Extender (LE) probe for
      detection of VT genotypes of citrus pathogen
      Citrus tristeza virus (CTV), CTV-VT target

<400> SEQUENCE: 58
cgacagagcg gggacgta                                                  18

<210> SEQ ID NO 59
<211> LENGTH: 23
<212> TYPE: DNA
<213> ORGANISM: Artificial Sequence
<220> FEATURE:

<223> OTHER INFORMATION: synthetic VT021 Label Extender (LE) probe for
      detection of VT genotypes of citrus pathogen
      Citrus tristeza virus (CTV), CTV-VT target

<400> SEQUENCE: 59
gcagtaaggg gaggtttaca cag                                          23

<210> SEQ ID NO 60
<211> LENGTH: 17
<212> TYPE: DNA
<213> ORGANISM: Artificial Sequence
<220> FEATURE:
<223> OTHER INFORMATION: synthetic VT022 Label Extender (LE) probe for
      detection of VT genotypes of citrus pathogen
      Citrus tristeza virus (CTV), CTV-VT target

<400> SEQUENCE: 60
tggacttctt ggcggcg                                                 17

<210> SEQ ID NO 61
<211> LENGTH: 19
<212> TYPE: DNA
<213> ORGANISM: Artificial Sequence
<220> FEATURE:
<223> OTHER INFORMATION: synthetic VT023 Label Extender (LE) probe for
      detection of VT genotypes of citrus pathogen
      Citrus tristeza virus (CTV), CTV-VT target

<400> SEQUENCE: 61
tctttcttcg ccttgcgaa                                               19

<210> SEQ ID NO 62
<211> LENGTH: 22
<212> TYPE: DNA
<213> ORGANISM: Artificial Sequence
<220> FEATURE:
<223> OTHER INFORMATION: synthetic VT024 Label Extender (LE) probe for
      detection of VT genotypes of citrus pathogen
      Citrus tristeza virus (CTV), CTV-VT target

<400> SEQUENCE: 62
ccggctaaga aagaaagcag aa                                           22

<210> SEQ ID NO 63
<211> LENGTH: 17
<212> TYPE: DNA
<213> ORGANISM: Artificial Sequence
<220> FEATURE:
<223> OTHER INFORMATION: synthetic VT025 Label Extender (LE) probe for
      detection of VT genotypes of citrus pathogen
      Citrus tristeza virus (CTV), CTV-VT target

<400> SEQUENCE: 63
cgtgccgcag gggactt                                                 17

<210> SEQ ID NO 64
<211> LENGTH: 21
<212> TYPE: DNA
<213> ORGANISM: Artificial Sequence
<220> FEATURE:
<223> OTHER INFORMATION: synthetic VT026 Label Extender (LE) probe for
      detection of VT genotypes of citrus pathogen
      Citrus tristeza virus (CTV), CTV-VT target

<400> SEQUENCE: 64
gcgcctacga agtctatgac g                                            21

```
<210> SEQ ID NO 65
<211> LENGTH: 26
<212> TYPE: DNA
<213> ORGANISM: Artificial Sequence
<220> FEATURE:
<223> OTHER INFORMATION: synthetic VT027 Label Extender (LE) probe for
      detection of VT genotypes of citrus pathogen
      Citrus tristeza virus (CTV), CTV-VT target

<400> SEQUENCE: 65
atggtagggt ctactcgttt cataac                                          26

<210> SEQ ID NO 66
<211> LENGTH: 20
<212> TYPE: DNA
<213> ORGANISM: Artificial Sequence
<220> FEATURE:
<223> OTHER INFORMATION: synthetic VT028 Label Extender (LE) probe for
      detection of VT genotypes of citrus pathogen
      Citrus tristeza virus (CTV), CTV-VT target

<400> SEQUENCE: 66
cgtcttgggg actctcgtgc                                                 20

<210> SEQ ID NO 67
<211> LENGTH: 23
<212> TYPE: DNA
<213> ORGANISM: Artificial Sequence
<220> FEATURE:
<223> OTHER INFORMATION: synthetic VT029 Blocking Probe (BL) for
      detection of VT genotypes of citrus pathogen Citrus tristeza
      virus (CTV), CTV-VT target

<400> SEQUENCE: 67
agctccgagt ttcgacatgt tat                                             23

<210> SEQ ID NO 68
<211> LENGTH: 21
<212> TYPE: DNA
<213> ORGANISM: Artificial Sequence
<220> FEATURE:
<223> OTHER INFORMATION: synthetic VT030 Blocking Probe (BL) for
      detection of VT genotypes of citrus pathogen Citrus tristeza
      virus (CTV), CTV-VT target

<400> SEQUENCE: 68
aaacaggatt tccgtagagg g                                               21

<210> SEQ ID NO 69
<211> LENGTH: 18
<212> TYPE: DNA
<213> ORGANISM: Artificial Sequence
<220> FEATURE:
<223> OTHER INFORMATION: synthetic VT031 Blocking Probe (BL) for
      detection of VT genotypes of citrus pathogen Citrus tristeza
      virus (CTV), CTV-VT target

<400> SEQUENCE: 69
gcgcgaacag aaaacgga                                                   18

<210> SEQ ID NO 70
<211> LENGTH: 22
<212> TYPE: DNA
<213> ORGANISM: Artificial Sequence
<220> FEATURE:
<223> OTHER INFORMATION: synthetic VT032 Blocking Probe (BL) for
      detection of VT genotypes of citrus pathogen Citrus tristeza
      virus (CTV), CTV-VT target
```

<400> SEQUENCE: 70
cccgtgagaa gagtgaagaa gc                                    22

<210> SEQ ID NO 71
<211> LENGTH: 18
<212> TYPE: DNA
<213> ORGANISM: Artificial Sequence
<220> FEATURE:
<223> OTHER INFORMATION: synthetic psoro001 Capture Extender (CE) probe
      for detection of citrus pathogen Citrus psorosis virus
      (CPsV) target

<400> SEQUENCE: 71
tggcgatggt gaagggcc                                         18

<210> SEQ ID NO 72
<211> LENGTH: 26
<212> TYPE: DNA
<213> ORGANISM: Artificial Sequence
<220> FEATURE:
<223> OTHER INFORMATION: synthetic psoro002 Capture Extender (CE) probe
      for detection of citrus pathogen Citrus psorosis virus
      (CPsV) target

<400> SEQUENCE: 72
aagaacaagg ggtttcagaa tgatag                                26

<210> SEQ ID NO 73
<211> LENGTH: 21
<212> TYPE: DNA
<213> ORGANISM: Artificial Sequence
<220> FEATURE:
<223> OTHER INFORMATION: synthetic psoro003 Capture Extender (CE) probe
      for detection of citrus pathogen Citrus psorosis virus
      (CPsV) target

<400> SEQUENCE: 73
agcctcactc cagatggcag a                                     21

<210> SEQ ID NO 74
<211> LENGTH: 26
<212> TYPE: DNA
<213> ORGANISM: Artificial Sequence
<220> FEATURE:
<223> OTHER INFORMATION: synthetic psoro004 Capture Extender (CE) probe
      for detection of citrus pathogen Citrus psorosis virus
      (CPsV) target

<400> SEQUENCE: 74
tcaattgcaa taagagattt tctgaa                                26

<210> SEQ ID NO 75
<211> LENGTH: 22
<212> TYPE: DNA
<213> ORGANISM: Artificial Sequence
<220> FEATURE:
<223> OTHER INFORMATION: synthetic psoro005 Capture Extender (CE) probe
      for detection of citrus pathogen Citrus psorosis virus
      (CPsV) target

<400> SEQUENCE: 75
ctcctgaatc cctgatgcca tt                                    22

<210> SEQ ID NO 76
<211> LENGTH: 24
<212> TYPE: DNA
<213> ORGANISM: Artificial Sequence

```
<220> FEATURE:
<223> OTHER INFORMATION: synthetic psoro006 Capture Extender (CE) probe
      for detection of citrus pathogen Citrus psorosis virus
      (CPsV) target

<400> SEQUENCE: 76
atctgtgaga tatgctgggt ttgc                                              24

<210> SEQ ID NO 77
<211> LENGTH: 23
<212> TYPE: DNA
<213> ORGANISM: Artificial Sequence
<220> FEATURE:
<223> OTHER INFORMATION: synthetic psoro007 Capture Extender (CE) probe
      for detection of citrus pathogen Citrus psorosis virus
      (CPsV) target

<400> SEQUENCE: 77
aacaaagaaa ttccctgcaa ggg                                               23

<210> SEQ ID NO 78
<211> LENGTH: 22
<212> TYPE: DNA
<213> ORGANISM: Artificial Sequence
<220> FEATURE:
<223> OTHER INFORMATION: synthetic psoro008 Capture Extender (CE) probe
      for detection of citrus pathogen Citrus psorosis virus
      (CPsV) target

<400> SEQUENCE: 78
gtgaggaatt gagccatgct cc                                                22

<210> SEQ ID NO 79
<211> LENGTH: 23
<212> TYPE: DNA
<213> ORGANISM: Artificial Sequence
<220> FEATURE:
<223> OTHER INFORMATION: synthetic psoro009 Label Extender (LE) probe
      for detection of citrus pathogen Citrus psorosis virus
      (CPsV) target

<400> SEQUENCE: 79
catggagtgt gttgacaaaa cca                                               23

<210> SEQ ID NO 80
<211> LENGTH: 25
<212> TYPE: DNA
<213> ORGANISM: Artificial Sequence
<220> FEATURE:
<223> OTHER INFORMATION: synthetic psoro010 Label Extender (LE) probe
      for detection of citrus pathogen Citrus psorosis virus
      (CPsV) target

<400> SEQUENCE: 80
attgacatgg ccgagaggat aataa                                             25

<210> SEQ ID NO 81
<211> LENGTH: 26
<212> TYPE: DNA
<213> ORGANISM: Artificial Sequence
<220> FEATURE:
<223> OTHER INFORMATION: synthetic psoro011 Label Extender (LE) probe
      for detection of citrus pathogen Citrus psorosis virus
      (CPsV) target

<400> SEQUENCE: 81
aaaaggcttc atcctttatc tgatga                                            26
```

<210> SEQ ID NO 82
<211> LENGTH: 23
<212> TYPE: DNA
<213> ORGANISM: Artificial Sequence
<220> FEATURE:
<223> OTHER INFORMATION: synthetic psoro012 Label Extender (LE) probe
      for detection of citrus pathogen Citrus psorosis virus
      (CPsV) target

<400> SEQUENCE: 82
tggagggaca atggaagaat cag 23

<210> SEQ ID NO 83
<211> LENGTH: 28
<212> TYPE: DNA
<213> ORGANISM: Artificial Sequence
<220> FEATURE:
<223> OTHER INFORMATION: synthetic psoro013 Label Extender (LE) probe
for detection of citrus pathogen Citrus psorosis virus
(CPsV) target

<400> SEQUENCE: 83
gctggaaacc aatcaaaaga ttgaaaaa 28

<210> SEQ ID NO 84
<211> LENGTH: 20
<212> TYPE: DNA
<213> ORGANISM: Artificial Sequence
<220> FEATURE:
<223> OTHER INFORMATION: synthetic psoro014 Label Extender (LE) probe
for detection of citrus pathogen Citrus psorosis virus
(CPsV) target

<400> SEQUENCE: 84
gtcccctgct gttggtgcaa 20

<210> SEQ ID NO 85
<211> LENGTH: 28
<212> TYPE: DNA
<213> ORGANISM: Artificial Sequence
<220> FEATURE:
<223> OTHER INFORMATION: synthetic psoro015 Label Extender (LE) probe
for detection of citrus pathogen Citrus psorosis virus
(CPsV) target

<400> SEQUENCE: 85
tgtttctcaa gattgatata gacaactt 28

<210> SEQ ID NO 86
<211> LENGTH: 27
<212> TYPE: DNA
<213> ORGANISM: Artificial Sequence
<220> FEATURE:
<223> OTHER INFORMATION: synthetic psoro016 Label Extender (LE) probe
for detection of citrus pathogen Citrus psorosis virus
(CPsV) target

<400> SEQUENCE: 86
gaagctgtat gatggtgatg taagttt 27

<210> SEQ ID NO 87
<211> LENGTH: 24
<212> TYPE: DNA
<213> ORGANISM: Artificial Sequence
<220> FEATURE:
<223> OTHER INFORMATION: synthetic CTLV001 Capture Extender (CE) probe
for detection of citrus pathogen Citrus tatter leaf
virus (CTLV) target

```
<400> SEQUENCE: 87
tgctgagagg gacctaaatc ctct                                          24

<210> SEQ ID NO 88
<211> LENGTH: 22
<212> TYPE: DNA
<213> ORGANISM: Artificial Sequence
<220> FEATURE:
<223> OTHER INFORMATION: synthetic CTLV002 Capture Extender (CE) probe
      for detection of citrus pathogen Citrus tatter leaf
      virus (CTLV) target

<400> SEQUENCE: 88
gggaggaacc gtcagaagtt cc                                            22

<210> SEQ ID NO 89
<211> LENGTH: 27
<212> TYPE: DNA
<213> ORGANISM: Artificial Sequence
<220> FEATURE:
<223> OTHER INFORMATION: synthetic CTLV003 Capture Extender (CE) probe
      for detection of citrus pathogen Citrus tatter leaf
      virus (CTLV) target

<400> SEQUENCE: 89
gtgattgcag agaagaaggt aaagctc                                       27

<210> SEQ ID NO 90
<211> LENGTH: 24
<212> TYPE: DNA
<213> ORGANISM: Artificial Sequence
<220> FEATURE:
<223> OTHER INFORMATION: synthetic CTLV004 Capture Extender (CE) probe
      for detection of citrus pathogen Citrus tatter leaf
      virus (CTLV) target

<400> SEQUENCE: 90
aagaaattca cgagccaaat cagc                                          24

<210> SEQ ID NO 91
<211> LENGTH: 22
<212> TYPE: DNA
<213> ORGANISM: Artificial Sequence
<220> FEATURE:
<223> OTHER INFORMATION: synthetic CTLV005 Capture Extender (CE) probe
      for detection of citrus pathogen Citrus tatter leaf
      virus (CTLV) target

<400> SEQUENCE: 91
caaaagcttt gggccatttc tt                                            22

<210> SEQ ID NO 92
<211> LENGTH: 20
<212> TYPE: DNA
<213> ORGANISM: Artificial Sequence
<220> FEATURE:
<223> OTHER INFORMATION: synthetic CTLV006 Capture Extender (CE) probe
      for detection of citrus pathogen Citrus tatter leaf
      virus (CTLV) target

<400> SEQUENCE: 92
cctgcctcga aaccccttt                                                20

<210> SEQ ID NO 93
<211> LENGTH: 26
<212> TYPE: DNA
```

-continued

<213> ORGANISM: Artificial Sequence
<220> FEATURE:
<223> OTHER INFORMATION: synthetic CTLV007 Label Extender (LE) probe for detection of citrus pathogen Citrus tatter leaf virus (CTLV) target

<400> SEQUENCE: 93
tgttgaagca cgtcttccaa actcat 26

<210> SEQ ID NO 94
<211> LENGTH: 25
<212> TYPE: DNA
<213> ORGANISM: Artificial Sequence
<220> FEATURE:
<223> OTHER INFORMATION: synthetic CTLV008 Label Extender (LE) probe for detection of citrus pathogen Citrus tatter leaf virus (CTLV) target

<400> SEQUENCE: 94
gaaactgggt cttatcagat gaccc 25

<210> SEQ ID NO 95
<211> LENGTH: 27
<212> TYPE: DNA
<213> ORGANISM: Artificial Sequence
<220> FEATURE:
<223> OTHER INFORMATION: synthetic CTLV009 Label Extender (LE) probe for detection of citrus pathogen Citrus tatter leaf virus (CTLV) target

<400> SEQUENCE: 95
agaagtagca gcaaaggttt tcaattc 27

<210> SEQ ID NO 96
<211> LENGTH: 24
<212> TYPE: DNA
<213> ORGANISM: Artificial Sequence
<220> FEATURE:
<223> OTHER INFORMATION: synthetic CTLV010 Label Extender (LE) probe for detection of citrus pathogen Citrus tatter leaf virus (CTLV) target

<400> SEQUENCE: 96
ttgtccttca gtacgaaaaa gcct 24

<210> SEQ ID NO 97
<211> LENGTH: 23
<212> TYPE: DNA
<213> ORGANISM: Artificial Sequence
<220> FEATURE:
<223> OTHER INFORMATION: synthetic CTLV011 Label Extender (LE) probe for detection of citrus pathogen Citrus tatter leaf virus (CTLV) target

<400> SEQUENCE: 97
cgactcctaa ccctccagtt cca 23

<210> SEQ ID NO 98
<211> LENGTH: 19
<212> TYPE: DNA
<213> ORGANISM: Artificial Sequence
<220> FEATURE:
<223> OTHER INFORMATION: synthetic CTLV012 Label Extender (LE) probe for detection of citrus pathogen Citrus tatter leaf virus (CTLV) target

<400> SEQUENCE: 98
cctgcaagac cgcgaccaa 19

<210> SEQ ID NO 99
<211> LENGTH: 25
<212> TYPE: DNA
<213> ORGANISM: Artificial Sequence
<220> FEATURE:
<223> OTHER INFORMATION: synthetic CTLV013 Label Extender (LE) probe for
      detection of citrus pathogen Citrus tatter leaf
      virus (CTLV) target

<400> SEQUENCE: 99
ttaagtataa aggcaggcat gtcaa                                         25

<210> SEQ ID NO 100
<211> LENGTH: 26
<212> TYPE: DNA
<213> ORGANISM: Artificial Sequence
<220> FEATURE:
<223> OTHER INFORMATION: synthetic CLBV001 Capture Extender (CE) probe
      for detection of citrus pathogen Citrus leaf blotch
      virus (CLBV) target

<400> SEQUENCE: 100
cagctctgaa ttttcgaatg atgtca                                        26

<210> SEQ ID NO 101
<211> LENGTH: 25
<212> TYPE: DNA
<213> ORGANISM: Artificial Sequence
<220> FEATURE:
<223> OTHER INFORMATION: synthetic CLBV002 Capture Extender (CE) probe
      for detection of citrus pathogen Citrus leaf blotch
      virus (CLBV) target

<400> SEQUENCE: 101
ttgagtgact cattcaattc ttcaa                                         25

<210> SEQ ID NO 102
<211> LENGTH: 19
<212> TYPE: DNA
<213> ORGANISM: Artificial Sequence
<220> FEATURE:
<223> OTHER INFORMATION: synthetic CLBV003 Capture Extender (CE) probe
      for detection of citrus pathogen Citrus leaf blotch
      virus (CLBV) target

<400> SEQUENCE: 102
cccagccaaa attgcagct                                                19

<210> SEQ ID NO 103
<211> LENGTH: 24
<212> TYPE: DNA
<213> ORGANISM: Artificial Sequence
<220> FEATURE:
<223> OTHER INFORMATION: synthetic CLBV004 Capture Extender (CE) probe
      for detection of citrus pathogen Citrus leaf blotch
      virus (CLBV) target

<400> SEQUENCE: 103
atctttggga aatgtctttc aact                                          24

<210> SEQ ID NO 104
<211> LENGTH: 25
<212> TYPE: DNA
<213> ORGANISM: Artificial Sequence
<220> FEATURE:
<223> OTHER INFORMATION: synthetic CLBV005 Capture Extender (CE) probe
      for detection of citrus pathogen Citrus leaf blotch virus (CLBV) target

<400> SEQUENCE: 104
gctcatgccc ttttttttc aaatt                                         25

<210> SEQ ID NO 105
<211> LENGTH: 23
<212> TYPE: DNA
<213> ORGANISM: Artificial Sequence
<220> FEATURE:
<223> OTHER INFORMATION: synthetic CLBV006 Capture Extender (CE) probe
      for detection of citrus pathogen Citrus leaf blotch
      virus (CLBV) target

<400> SEQUENCE: 105
tgaggaatgg ttcaactatg gct                                          23

<210> SEQ ID NO 106
<211> LENGTH: 25
<212> TYPE: DNA
<213> ORGANISM: Artificial Sequence
<220> FEATURE:
<223> OTHER INFORMATION: synthetic CLBV007 Label Extender (LE) probe for
      detection of citrus pathogen Citrus leaf blotch
      virus (CLBV) target

<400> SEQUENCE: 106
tcagaatttc tgtcctcatc agatg                                        25

<210> SEQ ID NO 107
<211> LENGTH: 19
<212> TYPE: DNA
<213> ORGANISM: Artificial Sequence
<220> FEATURE:
<223> OTHER INFORMATION: synthetic CLBV008 Label Extender (LE) probe for
      detection of citrus pathogen Citrus leaf blotch
      virus (CLBV) target

<400> SEQUENCE: 107
tctccatgct cggccacta                                               19

<210> SEQ ID NO 108
<211> LENGTH: 21
<212> TYPE: DNA
<213> ORGANISM: Artificial Sequence
<220> FEATURE:
<223> OTHER INFORMATION: synthetic CLBV009 Label Extender (LE) probe for
      detection of citrus pathogen Citrus leaf blotch
      virus (CLBV) target

<400> SEQUENCE: 108
tcagggtcca cctcctctgt g                                            21

<210> SEQ ID NO 109
<211> LENGTH: 23
<212> TYPE: DNA
<213> ORGANISM: Artificial Sequence
<220> FEATURE:
<223> OTHER INFORMATION: synthetic CLBV010 Label Extender (LE) probe for
      detection of citrus pathogen Citrus leaf blotch
      virus (CLBV) target

<400> SEQUENCE: 109
tgtgatctca agctgtgatg cat                                          23

<210> SEQ ID NO 110
<211> LENGTH: 24

```
<212> TYPE: DNA
<213> ORGANISM: Artificial Sequence
<220> FEATURE:
<223> OTHER INFORMATION: synthetic CLBV011 Label Extender (LE) probe for
      detection of citrus pathogen Citrus leaf blotch
      virus (CLBV) target

<400> SEQUENCE: 110
ttcaagctgc tgctctctat ctgc                                           24

<210> SEQ ID NO 111
<211> LENGTH: 19
<212> TYPE: DNA
<213> ORGANISM: Artificial Sequence
<220> FEATURE:
<223> OTHER INFORMATION: synthetic CLBV012 Label Extender (LE) probe for
      detection of citrus pathogen Citrus leaf blotch
      virus (CLBV) target

<400> SEQUENCE: 111
ccactgccgg tcagtggtt                                                 19

<210> SEQ ID NO 112
<211> LENGTH: 23
<212> TYPE: DNA
<213> ORGANISM: Artificial Sequence
<220> FEATURE:
<223> OTHER INFORMATION: synthetic CLBV013 Label Extender (LE) probe for
      detection of citrus pathogen Citrus leaf blotch
      virus (CLBV) target

<400> SEQUENCE: 112
cagcatgtac cggttcagaa gat                                            23

<210> SEQ ID NO 113
<211> LENGTH: 21
<212> TYPE: DNA
<213> ORGANISM: Artificial Sequence
<220> FEATURE:
<223> OTHER INFORMATION: synthetic CLBV014 Label Extender (LE) probe for
      detection of citrus pathogen Citrus leaf blotch
      virus (CLBV) target

<400> SEQUENCE: 113
actgtggagc gtgtgctgat t                                              21

<210> SEQ ID NO 114
<211> LENGTH: 21
<212> TYPE: DNA
<213> ORGANISM: Artificial Sequence
<220> FEATURE:
<223> OTHER INFORMATION: synthetic CLBV015 Label Extender (LE) probe for
      detection of citrus pathogen Citrus leaf blotch
      virus (CLBV) target

<400> SEQUENCE: 114
gcagatcatt caccacatgc a                                              21

<210> SEQ ID NO 115
<211> LENGTH: 22
<212> TYPE: DNA
<213> ORGANISM: Artificial Sequence
<220> FEATURE:
<223> OTHER INFORMATION: synthetic CLBV016 Blocking Probe (BL) for
      detection of citrus pathogen Citrus leaf blotch
      virus (CLBV) target

<400> SEQUENCE: 115
```

```
ggaaaaaatg gcgaagaaga cc                                                  22

<210> SEQ ID NO 116
<211> LENGTH: 26
<212> TYPE: DNA
<213> ORGANISM: Artificial Sequence
<220> FEATURE:
<223> OTHER INFORMATION: synthetic CLBV017 Blocking Probe (BL) for
      detection of citrus pathogen Citrus leaf blotch
      virus (CLBV) target

<400> SEQUENCE: 116 cttttttga ataaactctg ccgtac                                               26

<210> SEQ ID NO 117
<211> LENGTH: 25
<212> TYPE: DNA
<213> ORGANISM: Artificial Sequence
<220> FEATURE:
<223> OTHER INFORMATION: synthetic CLBV018 Blocking Probe (BL) for
      detection of citrus pathogen Citrus leaf blotch
      virus (CLBV) target

<400> SEQUENCE: 117
tgtttctcag atcttctgct tctgc                                               25

<210> SEQ ID NO 118
<211> LENGTH: 22
<212> TYPE: DNA
<213> ORGANISM: Artificial Sequence
<220> FEATURE:
<223> OTHER INFORMATION: synthetic CEVd001 Capture Extender (CE) probe
      for detection of citrus pathogen Citrus exocortis
      viroid (CEVd) target

<400> SEQUENCE: 118 tctttttct ttcctgcct gc                                                    22

<210> SEQ ID NO 119
<211> LENGTH: 20
<212> TYPE: DNA
<213> ORGANISM: Artificial Sequence
<220> FEATURE:
<223> OTHER INFORMATION: synthetic CEVd002 Capture Extender (CE) probe
      for detection of citrus pathogen Citrus exocortis
      viroid (CEVd) target

<400> SEQUENCE: 119
ggatccctga aggacttctt                                                     20

<210> SEQ ID NO 120
<211> LENGTH: 18
<212> TYPE: DNA
<213> ORGANISM: Artificial Sequence
<220> FEATURE:
<223> OTHER INFORMATION: synthetic CEVd003 Capture Extender (CE) probe
      for detection of citrus pathogen Citrus exocortis
      viroid (CEVd) target

<400> SEQUENCE: 120
tcctccaggt ttccccgg                                                       18

<210> SEQ ID NO 121
<211> LENGTH: 18
<212> TYPE: DNA
<213> ORGANISM: Artificial Sequence
<220> FEATURE:
<223> OTHER INFORMATION: synthetic CEVd004 Capture Extender (CE) probe
``` for detection of citrus pathogen Citrus exocortis
      viroid (CEVd) target

<400> SEQUENCE: 121
ttctccgctg gacgccag                                                  18

<210> SEQ ID NO 122
<211> LENGTH: 18
<212> TYPE: DNA
<213> ORGANISM: Artificial Sequence
<220> FEATURE:
<223> OTHER INFORMATION: synthetic CEVd005 Capture Extender (CE) probe
      for detection of citrus pathogen Citrus exocortis
      viroid (CEVd) target

<400> SEQUENCE: 122
cctcgcccgg agagcagt                                                  18

<210> SEQ ID NO 123
<211> LENGTH: 21
<212> TYPE: DNA
<213> ORGANISM: Artificial Sequence
<220> FEATURE:
<223> OTHER INFORMATION: synthetic CEVd006 Capture Extender (CE) probe
      for detection of citrus pathogen Citrus exocortis
      viroid (CEVd) target

<400> SEQUENCE: 123
tagggttccg agggctttca c                                              21

<210> SEQ ID NO 124
<211> LENGTH: 21
<212> TYPE: DNA
<213> ORGANISM: Artificial Sequence
<220> FEATURE:
<223> OTHER INFORMATION: synthetic CEVd007 Label Extender (LE) probe for
      detection of citrus pathogen Citrus exocortis
      viroid (CEVd) target

<400> SEQUENCE: 124
ggaacctcaa gaaagatccc g                                              21

<210> SEQ ID NO 125
<211> LENGTH: 20
<212> TYPE: DNA
<213> ORGANISM: Artificial Sequence
<220> FEATURE:
<223> OTHER INFORMATION: synthetic CEVd008 Label Extender (LE) probe for
      detection of citrus pathogen Citrus exocortis
      viroid (CEVd) target

<400> SEQUENCE: 125
agggtcaggt gagcaccaca                                                20

<210> SEQ ID NO 126
<211> LENGTH: 17
<212> TYPE: DNA
<213> ORGANISM: Artificial Sequence
<220> FEATURE:
<223> OTHER INFORMATION: synthetic CEVd009 Label Extender (LE) probe for
      detection of citrus pathogen Citrus exocortis
      viroid (CEVd) target

<400> SEQUENCE: 126 ccccccgac ctcgact                                                    17

<210> SEQ ID NO 127

```
<211> LENGTH: 16
<212> TYPE: DNA
<213> ORGANISM: Artificial Sequence
<220> FEATURE:
<223> OTHER INFORMATION: synthetic CEVd010 Label Extender (LE) probe for
      detection of citrus pathogen Citrus exocortis
      viroid (CEVd) target

<400> SEQUENCE: 127
tgatccgcgg cgaccg                                              16

<210> SEQ ID NO 128
<211> LENGTH: 23
<212> TYPE: DNA
<213> ORGANISM: Artificial Sequence
<220> FEATURE:
<223> OTHER INFORMATION: synthetic CEVd011 Label Extender (LE) probe for
      detection of citrus pathogen Citrus exocortis
      viroid (CEVd) target

<400> SEQUENCE: 128
aaaggaagga gacgagctcc tgt                                      23

<210> SEQ ID NO 129
<211> LENGTH: 19
<212> TYPE: DNA
<213> ORGANISM: Artificial Sequence
<220> FEATURE:
<223> OTHER INFORMATION: synthetic CEVd012 Label Extender (LE) probe for
      detection of citrus pathogen Citrus exocortis
      viroid (CEVd) target

<400> SEQUENCE: 129
ggatgtggag ccagcagcg                                           19

<210> SEQ ID NO 130
<211> LENGTH: 22
<212> TYPE: DNA
<213> ORGANISM: Artificial Sequence
<220> FEATURE:
<223> OTHER INFORMATION: synthetic CEVd013 Label Extender (LE) probe for
      detection of citrus pathogen Citrus exocortis
      viroid (CEVd) target

<400> SEQUENCE: 130
tcagttgttt ccaccgggta gt                                       22

<210> SEQ ID NO 131
<211> LENGTH: 19
<212> TYPE: DNA
<213> ORGANISM: Artificial Sequence
<220> FEATURE:
<223> OTHER INFORMATION: synthetic CEVd014 Label Extender (LE) probe for
      detection of citrus pathogen Citrus exocortis
      viroid (CEVd) target

<400> SEQUENCE: 131
gcggtttggg gttgaagct                                           19

<210> SEQ ID NO 132
<211> LENGTH: 20
<212> TYPE: DNA
<213> ORGANISM: Artificial Sequence
<220> FEATURE:
<223> OTHER INFORMATION: synthetic CVdII001 Capture Extender (CE) probe
      for detection of citrus pathogen Hop stunt viroid
      (HSVd) target

<400> SEQUENCE: 132
```
ttttctttgc ttgcccatgc                                              20

<210> SEQ ID NO 133
<211> LENGTH: 22
<212> TYPE: DNA
<213> ORGANISM: Artificial Sequence
<220> FEATURE:
<223> OTHER INFORMATION: synthetic CVdII002 Capture Extender (CE) probe
      for detection of citrus pathogen Hop stunt viroid
      (HSVd) target

<400> SEQUENCE: 133
ggattctgag aagagttgcc cc                                           22

<210> SEQ ID NO 134
<211> LENGTH: 24
<212> TYPE: DNA
<213> ORGANISM: Artificial Sequence
<220> FEATURE:
<223> OTHER INFORMATION: synthetic CVdII003 Capture Extender (CE) probe
      for detection of citrus pathogen Hop stunt viroid
      (HSVd) target

<400> SEQUENCE: 134
agctagaagc ctctactcca gagc                                         24

<210> SEQ ID NO 135
<211> LENGTH: 21
<212> TYPE: DNA
<213> ORGANISM: Artificial Sequence
<220> FEATURE:
<223> OTHER INFORMATION: synthetic CVdII004 Capture Extender (CE) probe
      for detection of citrus pathogen Hop stunt viroid
      (HSVd) target

<400> SEQUENCE: 135
ggacgatcga tggtgtttcg a                                            21

<210> SEQ ID NO 136
<211> LENGTH: 25
<212> TYPE: DNA
<213> ORGANISM: Artificial Sequence
<220> FEATURE:
<223> OTHER INFORMATION: synthetic CVdII005 Capture Extender (CE) probe
      for detection of citrus pathogen Hop stunt viroid
      (HSVd) target

<400> SEQUENCE: 136
agccaggaga aggtaaaaga agaag                                        25

<210> SEQ ID NO 137
<211> LENGTH: 20
<212> TYPE: DNA
<213> ORGANISM: Artificial Sequence
<220> FEATURE:
<223> OTHER INFORMATION: synthetic CVdII006 Capture Extender (CE) probe
      for detection of citrus pathogen Hop stunt viroid
      (HSVd) target

<400> SEQUENCE: 137
cgaaccgaga ggtgatgcca                                              20

<210> SEQ ID NO 138
<211> LENGTH: 21
<212> TYPE: DNA
<213> ORGANISM: Artificial Sequence
<220> FEATURE:

<223> OTHER INFORMATION: synthetic CVdII007 Label Extender (LE) probe
      for detection of citrus pathogen Hop stunt viroid
      (HSVd) target

<400> SEQUENCE: 138
ggcaactcga gaattcccca g                                              21

<210> SEQ ID NO 139
<211> LENGTH: 22
<212> TYPE: DNA
<213> ORGANISM: Artificial Sequence
<220> FEATURE:
<223> OTHER INFORMATION: synthetic CVdII008 Label Extender (LE) probe
      for detection of citrus pathogen Hop stunt viroid
      (HSVd) target

<400> SEQUENCE: 139
ggggctcctt tctcaggtaa gt                                         22

<210> SEQ ID NO 140
<211> LENGTH: 17
<212> TYPE: DNA
<213> ORGANISM: Artificial Sequence
<220> FEATURE:
<223> OTHER INFORMATION: synthetic CVdII009 Label Extender (LE) probe
      for detection of citrus pathogen Hop stunt viroid
      (HSVd) target

<400> SEQUENCE: 140
accgcggccc tctctcc                                               17

<210> SEQ ID NO 141
<211> LENGTH: 19
<212> TYPE: DNA
<213> ORGANISM: Artificial Sequence
<220> FEATURE:
<223> OTHER INFORMATION: synthetic CVdII010 Label Extender (LE) probe
      for detection of citrus pathogen Hop stunt viroid
      (HSVd) target

<400> SEQUENCE: 141
ccggtcgcgt ctcatcgga                                             19

<210> SEQ ID NO 142
<211> LENGTH: 24
<212> TYPE: DNA
<213> ORGANISM: Artificial Sequence
<220> FEATURE:
<223> OTHER INFORMATION: synthetic CVdII011 Label Extender (LE) probe
      for detection of citrus pathogen Hop stunt viroid
      (HSVd) target

<400> SEQUENCE: 142
ggcagaggct cagatagaca aaaa                                       24

<210> SEQ ID NO 143
<211> LENGTH: 20
<212> TYPE: DNA
<213> ORGANISM: Artificial Sequence
<220> FEATURE:
<223> OTHER INFORMATION: synthetic CVdII012 Label Extender (LE) probe
      for detection of citrus pathogen Hop stunt viroid
      (HSVd) target

<400> SEQUENCE: 143
gggctcaaga gaggatccgc                                            20

-continued

<210> SEQ ID NO 144
<211> LENGTH: 23
<212> TYPE: DNA
<213> ORGANISM: Artificial Sequence
<220> FEATURE:
<223> OTHER INFORMATION: synthetic leprosis3 Capture Extender (CE) probe
      for detection of citrus pathogen Citrus leprosis
      virus (CiLV) target

<400> SEQUENCE: 144
tgctaatatc acgcagacct tca                                            23

<210> SEQ ID NO 145
<211> LENGTH: 21
<212> TYPE: DNA
<213> ORGANISM: Artificial Sequence
<220> FEATURE:
<223> OTHER INFORMATION: synthetic leprosis9 Capture Extender (CE) probe
      for detection of citrus pathogen Citrus leprosis
      virus (CiLV) target

<400> SEQUENCE: 145
ggccttctgc ttagcaggtt t                                              21

<210> SEQ ID NO 146
<211> LENGTH: 19
<212> TYPE: DNA
<213> ORGANISM: Artificial Sequence
<220> FEATURE:
<223> OTHER INFORMATION: synthetic leprosis11 Capture Extender (CE)
      probe for detection of citrus pathogen Citrus leprosis
      virus (CiLV) target

<400> SEQUENCE: 146
tgggtggagc aagctgctt                                                 19

<210> SEQ ID NO 147
<211> LENGTH: 19
<212> TYPE: DNA
<213> ORGANISM: Artificial Sequence
<220> FEATURE:
<223> OTHER INFORMATION: synthetic leprosis14 Capture Extender (CE)
      probe for detection of citrus pathogen Citrus leprosis
      virus (CiLV) target

<400> SEQUENCE: 147
cggcatattt tgggcagtg                                                 19

<210> SEQ ID NO 148
<211> LENGTH: 25
<212> TYPE: DNA
<213> ORGANISM: Artificial Sequence
<220> FEATURE:
<223> OTHER INFORMATION: synthetic leprosis18 Capture Extender (CE)
      probe for detection of citrus pathogen Citrus leprosis
      virus (CiLV) target

<400> SEQUENCE: 148
gcttccatta ccttaaaatc aggta                                          25

<210> SEQ ID NO 149
<211> LENGTH: 22
<212> TYPE: DNA
<213> ORGANISM: Artificial Sequence
<220> FEATURE:
<223> OTHER INFORMATION: synthetic leprosis19 Capture Extender (CE)
      probe for detection of citrus pathogen Citrus leprosis
      virus (CiLV) target -continued

<400> SEQUENCE: 149
gacggcaact aggtcctcag aa    22

<210> SEQ ID NO 150
<211> LENGTH: 22
<212> TYPE: DNA
<213> ORGANISM: Artificial Sequence
<220> FEATURE:
<223> OTHER INFORMATION: synthetic leprosis1 Label Extender (LE) probe
      for detection of citrus pathogen Citrus leprosis virus
      (CiLV) target

<400> SEQUENCE: 150
ctcaatggcc tgcataatct ca    22

<210> SEQ ID NO 151
<211> LENGTH: 20
<212> TYPE: DNA
<213> ORGANISM: Artificial Sequence
<220> FEATURE:
<223> OTHER INFORMATION: synthetic leprosis2 Label Extender (LE) probe
      for detection of citrus pathogen Citrus leprosis virus
      (CiLV) target

<400> SEQUENCE: 151
ggaacagaca cgttgtgccg    20

<210> SEQ ID NO 152
<211> LENGTH: 24
<212> TYPE: DNA
<213> ORGANISM: Artificial Sequence
<220> FEATURE:
<223> OTHER INFORMATION: synthetic leprosis4 Label Extender (LE) probe
      for detection of citrus pathogen Citrus leprosis virus
      (CiLV) target

<400> SEQUENCE: 152
actgctgctt cttcttagta ggct    24

<210> SEQ ID NO 153
<211> LENGTH: 21
<212> TYPE: DNA
<213> ORGANISM: Artificial Sequence
<220> FEATURE:
<223> OTHER INFORMATION: synthetic leprosis5 Label Extender (LE) probe
      for detection of citrus pathogen Citrus leprosis virus
      (CiLV) target

<400> SEQUENCE: 153
gtgacagttg ttgaggttgc g    21

<210> SEQ ID NO 154
<211> LENGTH: 19
<212> TYPE: DNA
<213> ORGANISM: Artificial Sequence
<220> FEATURE:
<223> OTHER INFORMATION: synthetic leprosis7 Label Extender (LE) probe
      for detection of citrus pathogen Citrus leprosis virus
      (CiLV) target

<400> SEQUENCE: 154
ccgggttgca gttgctgag    19

<210> SEQ ID NO 155
<211> LENGTH: 22
<212> TYPE: DNA
<213> ORGANISM: Artificial Sequence

```
<220> FEATURE:
<223> OTHER INFORMATION: synthetic leprosis8 Label Extender (LE) probe
      for detection of citrus pathogen Citrus leprosis virus
      (CiLV) target

<400> SEQUENCE: 155
cttggcctga taaccactag ga                                              22

<210> SEQ ID NO 156
<211> LENGTH: 27
<212> TYPE: DNA
<213> ORGANISM: Artificial Sequence
<220> FEATURE:
<223> OTHER INFORMATION: synthetic leprosis16 Label Extender (LE) probe
      for detection of citrus pathogen Citrus leprosis virus
      (CiLV) target

<400> SEQUENCE: 156
ttataatatg tcatccctat ctgcttc                                         27

<210> SEQ ID NO 157
<211> LENGTH: 20
<212> TYPE: DNA
<213> ORGANISM: Artificial Sequence
<220> FEATURE:
<223> OTHER INFORMATION: synthetic leprosis17 Label Extender (LE) probe
      for detection of citrus pathogen Citrus leprosis virus
      (CiLV) target

<400> SEQUENCE: 157
acgcataggg ctcggatatc                                                 20

<210> SEQ ID NO 158
<211> LENGTH: 26
<212> TYPE: DNA
<213> ORGANISM: Artificial Sequence
<220> FEATURE:
<223> OTHER INFORMATION: synthetic leprosis21 Label Extender (LE) probe
      for detection of citrus pathogen Citrus leprosis virus
      (CiLV) target

<400> SEQUENCE: 158
atactatata agcgcttctc aaagct                                          26

<210> SEQ ID NO 159
<211> LENGTH: 17
<212> TYPE: DNA
<213> ORGANISM: Artificial Sequence
<220> FEATURE:
<223> OTHER INFORMATION: synthetic leprosis22 Label Extender (LE) probe
      for detection of citrus pathogen Citrus leprosis virus
      (CiLV) target

<400> SEQUENCE: 159
gtcgcttcgg gaagccc                                                    17

<210> SEQ ID NO 160
<211> LENGTH: 21
<212> TYPE: DNA
<213> ORGANISM: Artificial Sequence
<220> FEATURE:
<223> OTHER INFORMATION: synthetic leprosis23 Label Extender (LE) probe
      for detection of citrus pathogen Citrus leprosis virus
      (CiLV) target

<400> SEQUENCE: 160
ccgggacaac gttctttatg g                                               21
```

<210> SEQ ID NO 161
<211> LENGTH: 27
<212> TYPE: DNA
<213> ORGANISM: Artificial Sequence
<220> FEATURE:
<223> OTHER INFORMATION: synthetic leprosis24 Label Extender (LE) probe
      for detection of citrus pathogen Citrus leprosis virus
      (CiLV) target

<400> SEQUENCE: 161
caatgtagtg atcactgaac tcgaata                                           27

<210> SEQ ID NO 162
<211> LENGTH: 24
<212> TYPE: DNA
<213> ORGANISM: Artificial Sequence
<220> FEATURE:
<223> OTHER INFORMATION: synthetic Nad54 Capture Extender (CE) probe for
      detection of NADH dehydrogenase housekeeping
      citrus gene internal control target

<400> SEQUENCE: 162
ggtcattata gcggttcctt ctga                                              24

<210> SEQ ID NO 163
<211> LENGTH: 23
<212> TYPE: DNA
<213> ORGANISM: Artificial Sequence
<220> FEATURE:
<223> OTHER INFORMATION: synthetic Nad55 Capture Extender (CE) probe for
      detection of NADH dehydrogenase housekeeping
      citrus gene internal control target

<400> SEQUENCE: 163
gaagagaatg aaacgcacgt agt                                               23

<210> SEQ ID NO 164
<211> LENGTH: 22
<212> TYPE: DNA
<213> ORGANISM: Artificial Sequence
<220> FEATURE:
<223> OTHER INFORMATION: synthetic Nad59 Capture Extender (CE) probe for
      detection of NADH dehydrogenase housekeeping
      citrus gene internal control target

<400> SEQUENCE: 164
caaacatttc cgatgagatc ca                                                22

<210> SEQ ID NO 165
<211> LENGTH: 25
<212> TYPE: DNA
<213> ORGANISM: Artificial Sequence
<220> FEATURE:
<223> OTHER INFORMATION: synthetic Nad515 Capture Extender (CE) probe
      for detection of NADH dehydrogenase housekeeping
      citrus gene internal control target

<400> SEQUENCE: 165
aataacacat aaatcgaggg ctatg                                             25

<210> SEQ ID NO 166
<211> LENGTH: 25
<212> TYPE: DNA
<213> ORGANISM: Artificial Sequence
<220> FEATURE:
<223> OTHER INFORMATION: synthetic Nad519 Capture Extender (CE) probe
      for detection of NADH dehydrogenase housekeeping
      citrus gene internal control target

<400> SEQUENCE: 166
aaatatgaag caagacctac tccct                                      25

<210> SEQ ID NO 167
<211> LENGTH: 22
<212> TYPE: DNA
<213> ORGANISM: Artificial Sequence
<220> FEATURE:
<223> OTHER INFORMATION: synthetic Nad522 Capture Extender (CE) probe
      for detection of NADH dehydrogenase housekeeping
      citrus gene internal control target

<400> SEQUENCE: 167
ctcgattgac aggcatagct tt                                         22

<210> SEQ ID NO 168
<211> LENGTH: 26
<212> TYPE: DNA
<213> ORGANISM: Artificial Sequence
<220> FEATURE:
<223> OTHER INFORMATION: synthetic Nad51 Label Extender (LE) probe for
      detection of NADH dehydrogenase housekeeping
      citrus gene internal control target

<400> SEQUENCE: 168
gggcaaaaat acgataagta gataca                                     26

<210> SEQ ID NO 169
<211> LENGTH: 22
<212> TYPE: DNA
<213> ORGANISM: Artificial Sequence
<220> FEATURE:
<223> OTHER INFORMATION: synthetic Nad52 Label Extender (LE) probe for
      detection of NADH dehydrogenase housekeeping
      citrus gene internal control target

<400> SEQUENCE: 169
ctgctacgga actaccgaga ag                                         22

<210> SEQ ID NO 170
<211> LENGTH: 27
<212> TYPE: DNA
<213> ORGANISM: Artificial Sequence
<220> FEATURE:
<223> OTHER INFORMATION: synthetic Nad56 Label Extender (LE) probe for
      detection of NADH dehydrogenase housekeeping
      citrus gene internal control target

<400> SEQUENCE: 170
tcataaaaag caatcagaga taagatc                                    27

<210> SEQ ID NO 171
<211> LENGTH: 19
<212> TYPE: DNA
<213> ORGANISM: Artificial Sequence
<220> FEATURE:
<223> OTHER INFORMATION: synthetic Nad57 Label Extender (LE) probe for
      detection of NADH dehydrogenase housekeeping
      citrus gene internal control target

<400> SEQUENCE: 171
actagctccc ggtgcgact                                             19

<210> SEQ ID NO 172
<211> LENGTH: 20
<212> TYPE: DNA

```
<213> ORGANISM: Artificial Sequence
<220> FEATURE:
<223> OTHER INFORMATION: synthetic Nad510 Label Extender (LE) probe for
      detection of NADH dehydrogenase housekeeping
      citrus gene internal control target

<400> SEQUENCE: 172
caagaagccc caagaagcat                                                20

<210> SEQ ID NO 173
<211> LENGTH: 20
<212> TYPE: DNA
<213> ORGANISM: Artificial Sequence
<220> FEATURE:
<223> OTHER INFORMATION: synthetic Nad511 Label Extender (LE) probe for
      detection of NADH dehydrogenase housekeeping
      citrus gene internal control target

<400> SEQUENCE: 173
actacggtcg ggctatcgaa                                                20

<210> SEQ ID NO 174
<211> LENGTH: 27
<212> TYPE: DNA
<213> ORGANISM: Artificial Sequence
<220> FEATURE:
<223> OTHER INFORMATION: synthetic Nad512 Label Extender (LE) probe for
      detection of NADH dehydrogenase housekeeping
      citrus gene internal control target

<400> SEQUENCE: 174
cttatggatg taaccacaat taacatc                                        27

<210> SEQ ID NO 175
<211> LENGTH: 23
<212> TYPE: DNA
<213> ORGANISM: Artificial Sequence
<220> FEATURE:
<223> OTHER INFORMATION: synthetic Nad513 Label Extender (LE) probe for
      detection of NADH dehydrogenase housekeeping
      citrus gene internal control target

<400> SEQUENCE: 175
tggaataaag atggaccaag cta                                            23

<210> SEQ ID NO 176
<211> LENGTH: 25
<212> TYPE: DNA
<213> ORGANISM: Artificial Sequence
<220> FEATURE:
<223> OTHER INFORMATION: synthetic Nad517 Label Extender (LE) probe for
      detection of NADH dehydrogenase housekeeping
      citrus gene internal control target

<400> SEQUENCE: 176
gagagttatc tccagtcacc aacat                                          25

<210> SEQ ID NO 177
<211> LENGTH: 21
<212> TYPE: DNA
<213> ORGANISM: Artificial Sequence
<220> FEATURE:
<223> OTHER INFORMATION: synthetic Nad518 Label Extender (LE) probe for
      detection of NADH dehydrogenase housekeeping
      citrus gene internal control target

<400> SEQUENCE: 177
cccatcccag gaataattga a                                              21
```

```
<210> SEQ ID NO 178
<211> LENGTH: 26
<212> TYPE: DNA
<213> ORGANISM: Artificial Sequence
<220> FEATURE:
<223> OTHER INFORMATION: synthetic Nad520 Label Extender (LE) probe for
      detection of NADH dehydrogenase housekeeping
      citrus gene internal control target

<400> SEQUENCE: 178
gtcgtgtaaa ccagaaatga attaac                                          26

<210> SEQ ID NO 179
<211> LENGTH: 23
<212> TYPE: DNA
<213> ORGANISM: Artificial Sequence
<220> FEATURE:
<223> OTHER INFORMATION: synthetic Nad521 Label Extender (LE) probe for
      detection of NADH dehydrogenase housekeeping
      citrus gene internal control target

<400> SEQUENCE: 179
tgtagctgct ttatctgcct gaa                                             23
```